US010946109B2

(12) United States Patent
Maeda et al.

(10) Patent No.: US 10,946,109 B2
(45) Date of Patent: Mar. 16, 2021

(54) POLYMER-TYPE FLUORESCENT MOLECULE PROBE

(71) Applicant: Hiroshi Maeda, Kumamoto (JP)

(72) Inventors: Hiroshi Maeda, Kumamoto (JP); Makoto Hashizume, Fukuoka (JP); Jun Fang, Kumamoto (JP); Hideaki Nakamura, Kumamoto (JP); Haibo Qin, Guangxi Province (CN); Steffen Hackbarth, Berlin (DE); Masaharu Murata, Fukuoka (JP)

(73) Assignee: HIROSHI MAEDA, Kumamoto (JP)

( * ) Notice: Subject to any disclaimer, the term of this patent is extended or adjusted under 35 U.S.C. 154(b) by 0 days.

(21) Appl. No.: 15/488,952

(22) Filed: Apr. 17, 2017

(65) Prior Publication Data

US 2017/0280984 A1 Oct. 5, 2017

Related U.S. Application Data

(62) Division of application No. 14/342,879, filed as application No. PCT/JP2012/072640 on Sep. 5, 2012, now Pat. No. 9,636,426.

(30) Foreign Application Priority Data

Sep. 5, 2011 (JP) ............................. JP2011-193237

(51) Int. Cl.

| | |
|---|---|
| ***A61B 1/04*** | (2006.01) |
| ***A61K 49/00*** | (2006.01) |
| ***A61B 1/313*** | (2006.01) |
| ***G01N 21/33*** | (2006.01) |
| ***G01N 21/64*** | (2006.01) |
| ***A61K 41/00*** | (2020.01) |
| ***G01N 33/574*** | (2006.01) |
| ***G01N 33/58*** | (2006.01) |
| ***A61K 47/58*** | (2017.01) |

(52) U.S. Cl.

CPC .......... *A61K 49/0082* (2013.01); *A61B 1/043* (2013.01); *A61B 1/313* (2013.01); *A61K 41/0057* (2013.01); *A61K 41/0071* (2013.01); *A61K 47/58* (2017.08); *A61K 49/0034* (2013.01); *A61K 49/0054* (2013.01); *G01N 21/33* (2013.01); *G01N 21/6447* (2013.01); *G01N 33/574* (2013.01); *G01N 33/582* (2013.01); *G01N 33/585* (2013.01); *A61K 49/005* (2013.01); *A61K 49/0017* (2013.01); *A61K 49/0036* (2013.01)

(58) Field of Classification Search

CPC ................ A61K 49/0082; A61K 47/58; A61K 49/0036; A61K 49/0054; G01N 33/582

See application file for complete search history.

(56) References Cited

U.S. PATENT DOCUMENTS

| | | | | |
|---|---|---|---|---|
| 3,557,065 | A * | 1/1971 | Blumberg | C08F 8/00 525/383 |
| 4,315,998 | A * | 2/1982 | Neckers | C08F 2/48 525/359.3 |
| 5,258,453 | A | 11/1993 | Kopecek et al. | |
| 6,217,848 | B1 | 4/2001 | Achilefu et al. | |
| 6,423,547 | B1 | 7/2002 | Rajagopalan et al. | |
| 7,662,360 | B2 * | 2/2010 | Patel | A61K 41/009 424/1.11 |
| 8,128,959 | B2 | 3/2012 | Maeda et al. | |
| 2002/0037254 | A1 | 3/2002 | Sinn et al. | |
| 2002/0122805 | A1 * | 9/2002 | Hasan | A61K 41/0057 424/178.1 |
| 2004/0147508 | A1 | 7/2004 | Brown et al. | |
| 2004/0234495 | A1 | 11/2004 | Maeda et al. | |
| 2005/0208136 | A1 | 9/2005 | Maeda et al. | |
| 2005/0287114 | A1 * | 12/2005 | Wang | A61K 31/785 424/78.27 |
| 2007/0086975 | A1 | 4/2007 | Ignatious | |
| 2009/0053247 | A1 | 2/2009 | Deonarain et al. | |
| 2009/0062476 | A1 | 3/2009 | Maeda et al. | |
| 2009/0209508 | A1 * | 8/2009 | Lange | B82Y 5/00 514/185 |
| 2010/0184955 | A1 | 7/2010 | Kim | |
| 2011/0064658 | A1 | 3/2011 | Scherz et al. | |
| 2013/0142734 | A1 * | 6/2013 | David | A61K 49/0032 424/9.6 |

FOREIGN PATENT DOCUMENTS

| | | |
|---|---|---|
| JP | 8-500327 | 1/1996 |
| JP | 2001-513583 | 9/2001 |
| JP | 2002-531377 | 9/2002 |

(Continued)

OTHER PUBLICATIONS

English translation of International Preliminary Report on Patentability and Written Opinion dated Mar. 12, 2014.

C. Leaf, "Why We're Losing the War on Cancer (and How to Win It)", Fortune, Mar. 22, 2004, pp. 1-17.

Y. Matsumura et al., "A New Concept for Macromolecular Therapeutics in Cancer Chemotherapy: Mechanism of Tumoritropic Accumulation of Proteins and the Antitumor Agent Smancs[1]", Cancer Research, vol. 46, pp. 6387-6392, Dec. 1986.

H. Maeda, "SMANCS and Polymer-Conjugated Macromolecular Drugs: Advantages in Cancer Chemotherapy", Advanced Drug Delivery Reviews, vol. 6, pp. 181-202, 1991.

(Continued)

*Primary Examiner* — James W Rogers

(74) *Attorney, Agent, or Firm* — Wenderoth, Lind & Ponack, L.L.P.

(57) ABSTRACT

The present invention provides a fluorescent molecular probe for efficient fluorescent detection (visualization) of tumors or for implementing fluorescent detection and photodynamic treatment, more specifically, the present invention provides a macromolecular fluorescent molecular probe for fluorescent detection of tumor, comprising a complex comprising a fluorescent molecule and a biocompatible macromolecule.

6 Claims, 13 Drawing Sheets

(56) References Cited

FOREIGN PATENT DOCUMENTS

| | | |
|---|---|---|
| JP | 2003-500367 | 1/2003 |
| JP | 2003-73273 | 3/2003 |
| JP | 2005-500271 | 1/2005 |
| JP | 2007-320902 | 12/2007 |
| JP | 2009-511456 | 3/2009 |
| JP | 2011-513298 | 4/2011 |
| WO | 2004/103409 | 12/2004 |
| WO | 2006/112361 | 10/2006 |
| WO | 2006/112362 | 10/2006 |

OTHER PUBLICATIONS

H. Maeda et al., "Mechanism of Tumor-Targeted Delivery of Macromolecular Drugs, Including the EPR Effect in Solid Tumor and Clinical Overview of the Prototype Polymeric Drug SMANCS", Journal of Controlled Release, vol. 74, pp. 47-61, 2001.

H. Maeda, "Tumor-Selective Delivery of Macromolecular Drugs via the EPR Effect: Background and Future Prospects", Bioconjugate Chemistry, vol. 21, No. 5, pp. 797-802, 2010.

Extended European Search Report dated May 28, 2015, issued in corresponding European Patent Application No. 12829505.2.

Arun K. Iyer, et al., "High-loading nanosized micelles of copoly(styrene-maleic acid)-zinc protoporphyrin for targeted delivery of a potent heme oxygenase inhibitor", Biomaterials, vol. 28, No. 10, Jan. 23, 2007, pp. 1871-1881.

Mašek et al., "Interaction of N-(2-Hydroxypropyl)methacrylamide Copolymer-Doxorubicin Conjugates with Human Liver Microsomal Cytochromes P450: Comparison with Free Doxorubicin", Drug Metabolism and Disposition, 2011, vol. 39, No. 9, pp. 1704-1710.

Twan Lammers, "Improving the efficacy of combined modality anticancer therapy using HPMA copolymer-based nanomedicine formulations", Advance Drug Delivery Reviews, 2010, vol. 62, pp. 203-230.

Michael F. Grahn et al., "In vivo photodynamic activity of mTHPC poly(ethylene glycol) conjugates (SC102)", The International Society for Optical Engineering, 2007, vol. 3191, pp. 180-186.

* cited by examiner

[Figure 1]
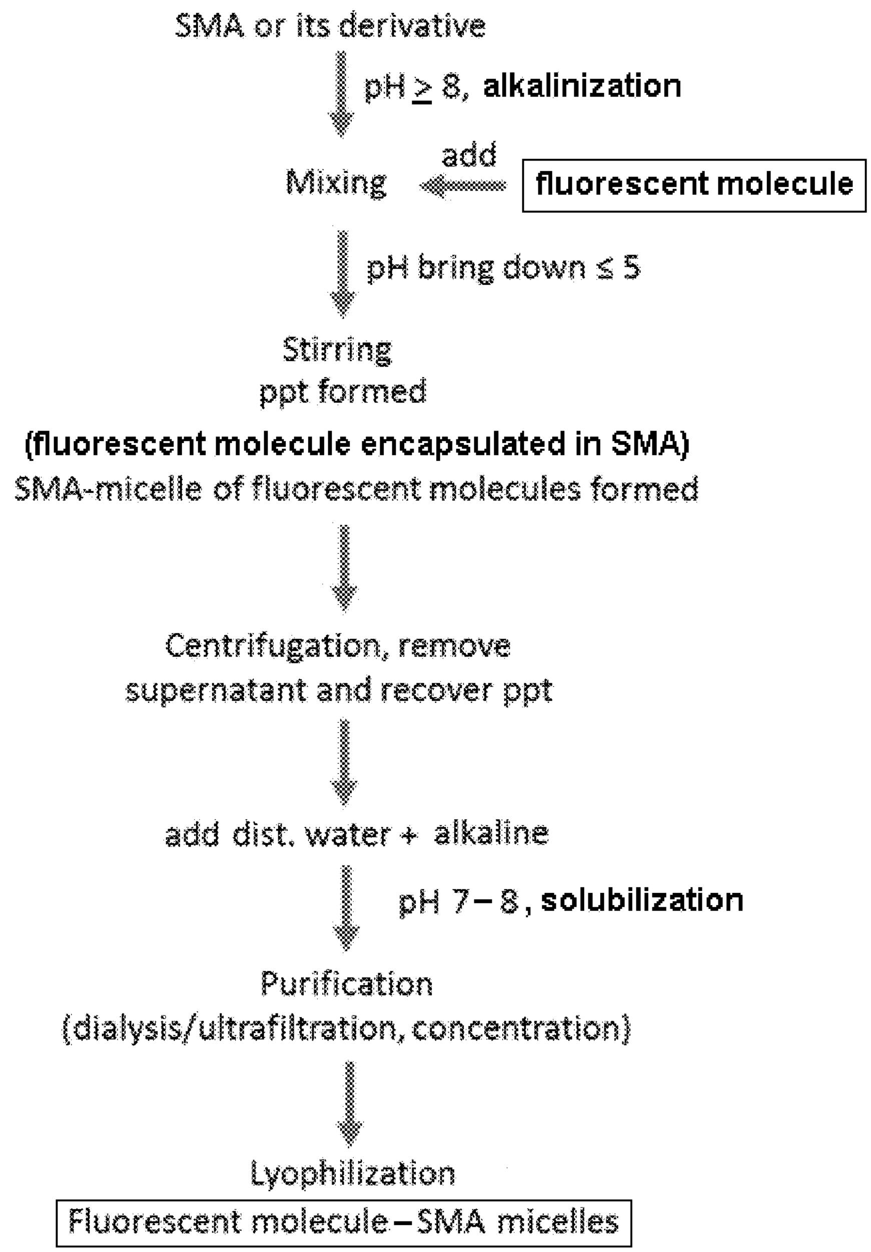
Figure 1. Flow chart of preparation of fluorescent molecule-SMA micelle.

[Figure 2]
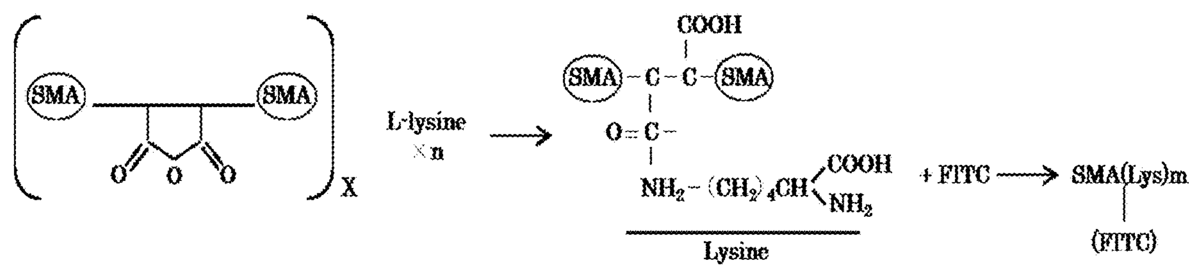
Figure 2. Reaction scheme of a complex wherein the fluorescent molecule is covalently bound to the SMA via lysine, and where excess lysine is added, m moles of lysine are conjugated to SMA.
[Figure 3]
(A)
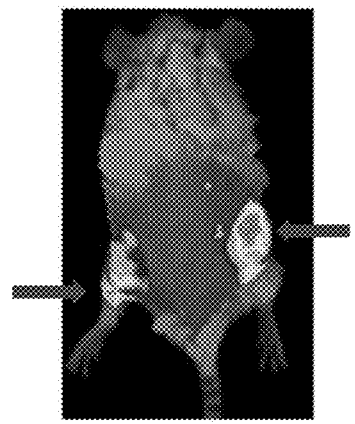
S-180 tumor Rhodamine-BSA i.v
(B)
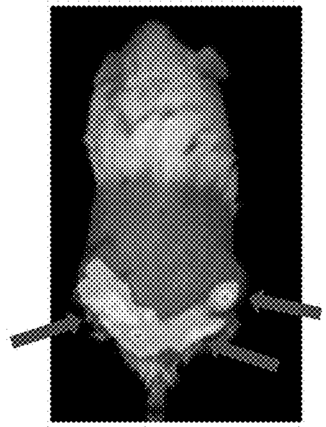
S-180 tumor SMA-ICG micelle i.v.
Figure 3. Bright areas both right and left sides shown by arrows indicate tumor areas.

[Figure 4]
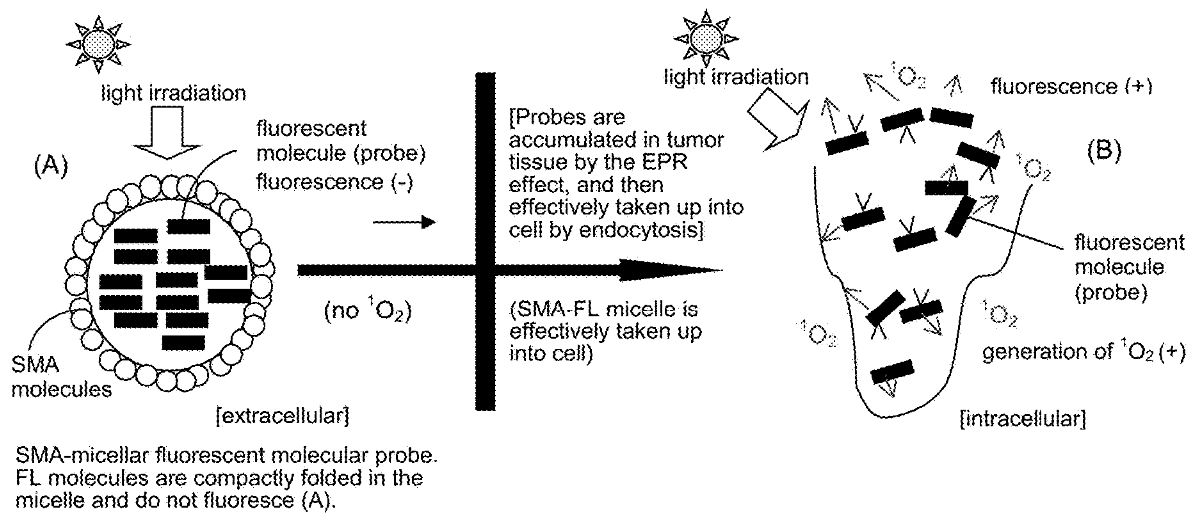
Figure 4. Conceptual picture of fluorescence generation and singlet oxygen [$^1O_2$] upon light irradiation.

[Figure 5]
(A)
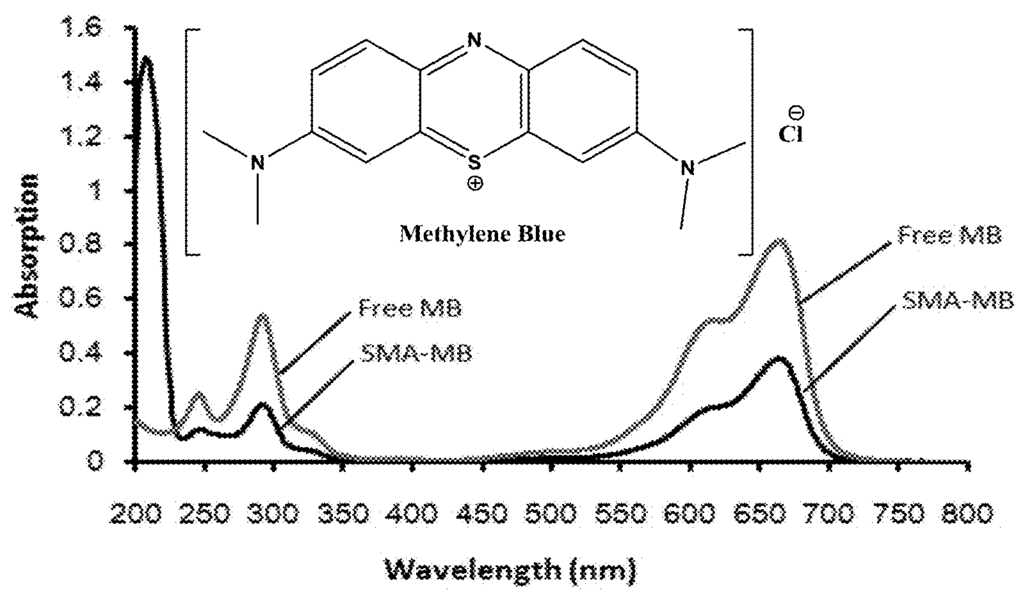
(B)
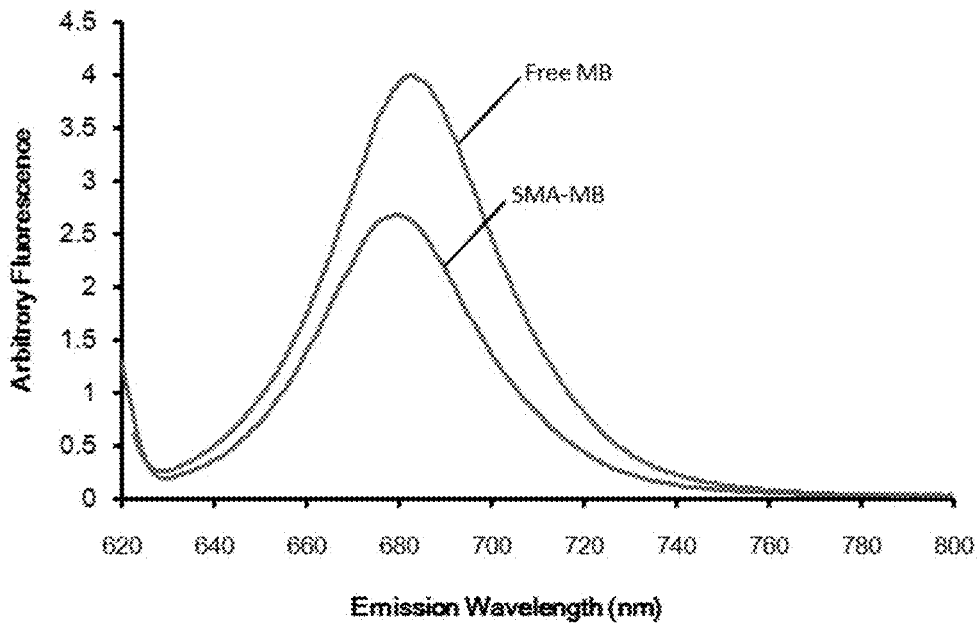
Figure 5. Spectroscopic characters of SMA micelles encapsulating methylene blue (MB) (SMA-MB micelles)

[Figure 6]
(A) Absorption spectra of SMA-ICG micelles.
(a) in 0.1M phosphate buffer pH 7.4 at 100 μg/ml.
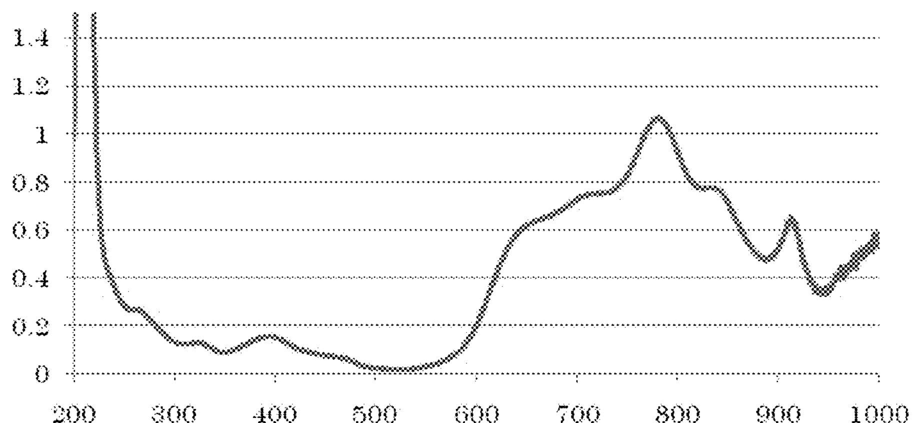
(b) in dimethylsulfoxide (DMSA) 25 μg/ml.
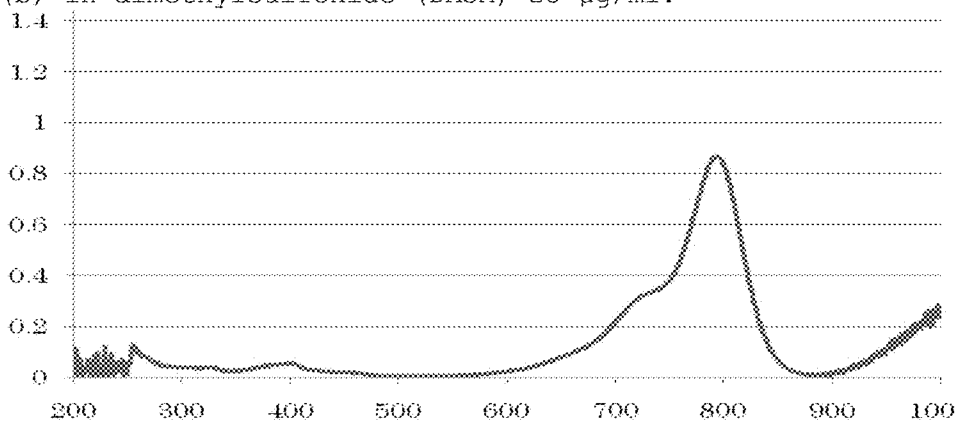
(B) Fluorescence spectrum of SMA-ICG micelles in 0.1M K phosphate buffer at 5 μg/ml excited at 765.
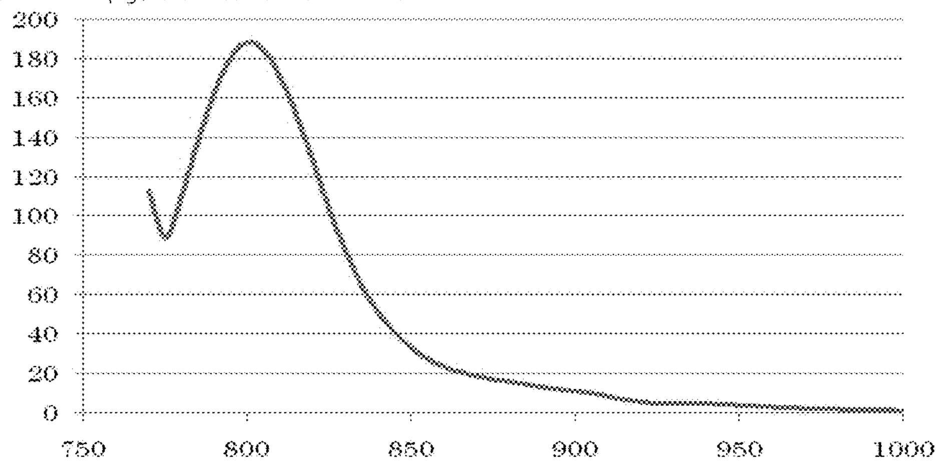
Figure 6. Spectroscopic characters of SMA micelles encapsulating indocyaninegreen (ICG) (SMA-ICG micelles)

[Figure 7]
(A)
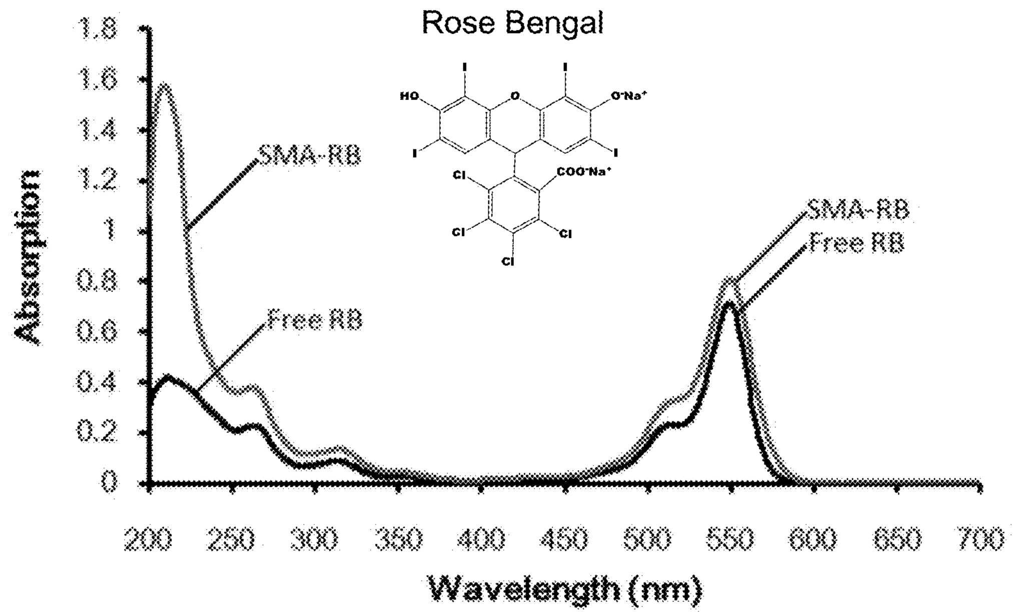
(B)
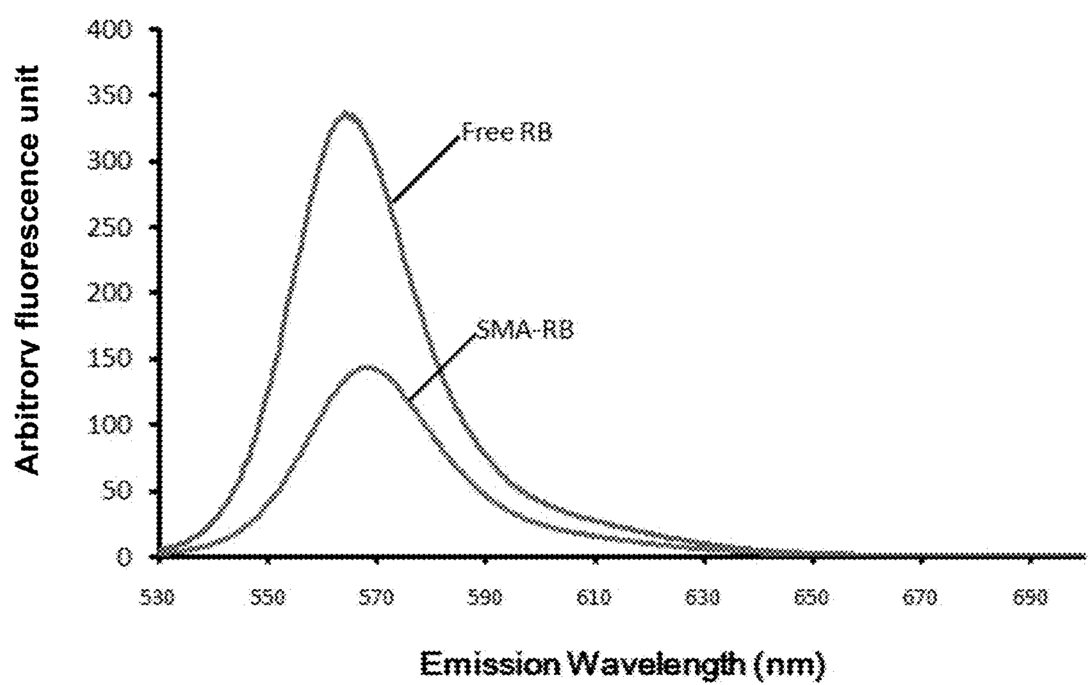
Figure 7. Spectroscopic characters of SMA micelles encapsulating rose bengal (RB) (SMA-RB micelles)

[Figure 8]
(A)
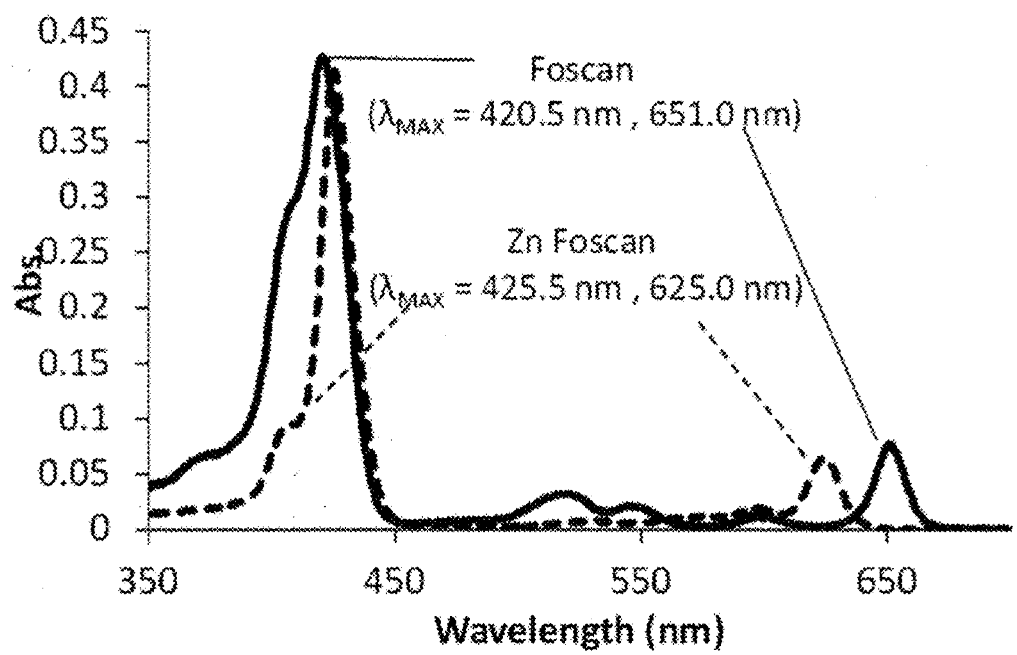
(B)
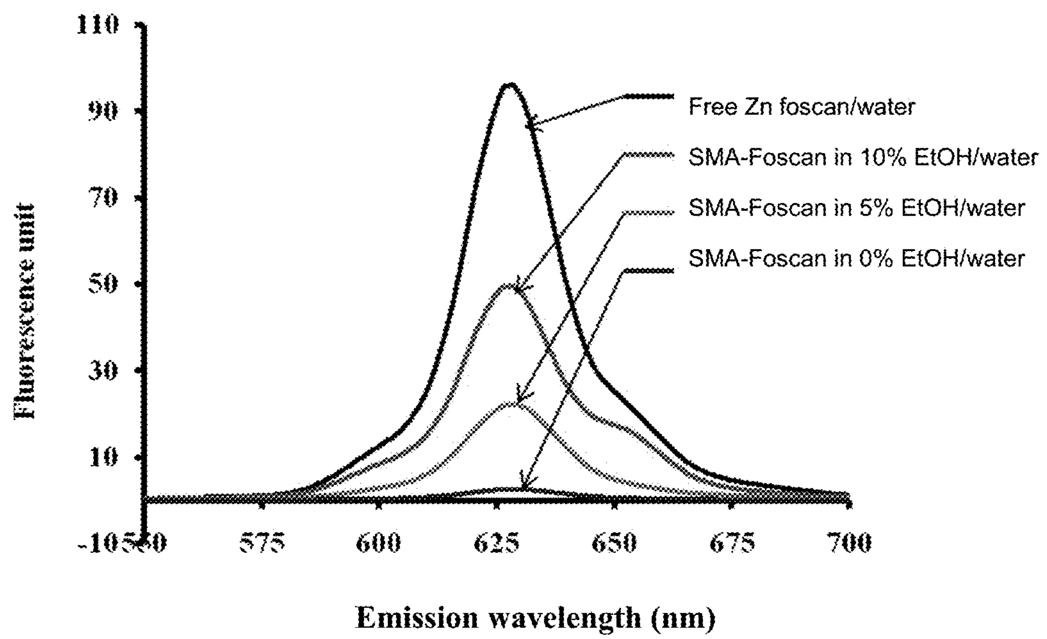
Figure 8. Spectroscopic characters of SMA micelles encapsulating Zn foscan (SMA-Zn foscan micelles)

[Figure 9]
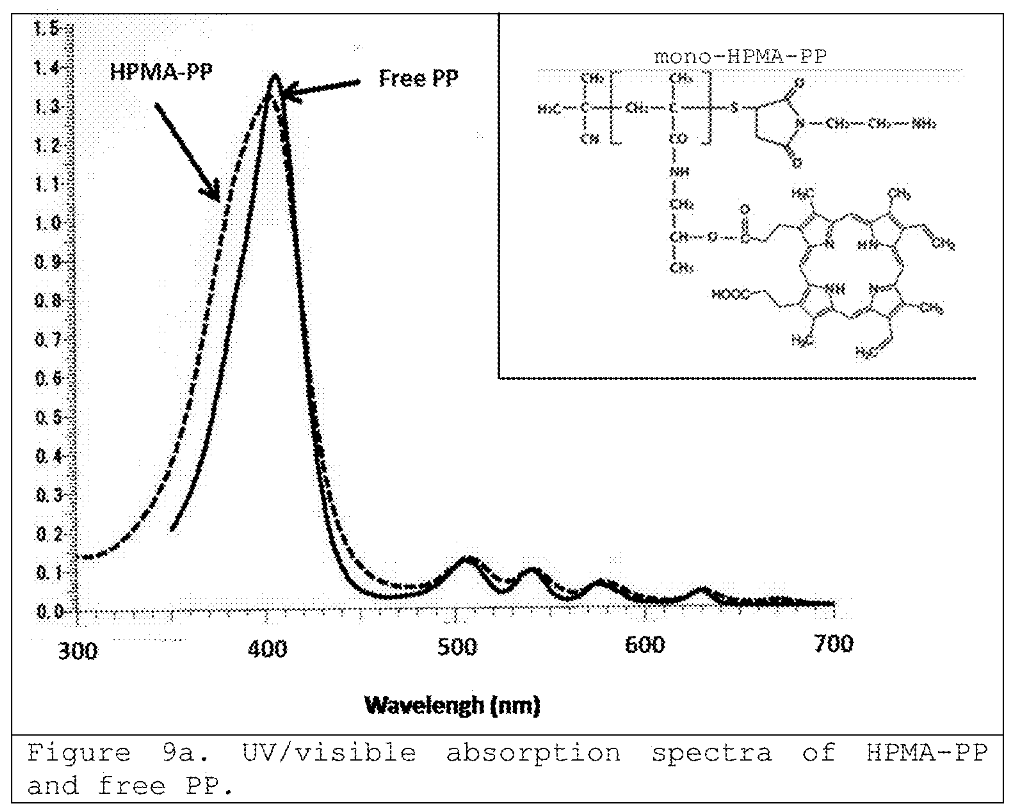
Figure 9a. UV/visible absorption spectra of HPMA-PP and free PP.
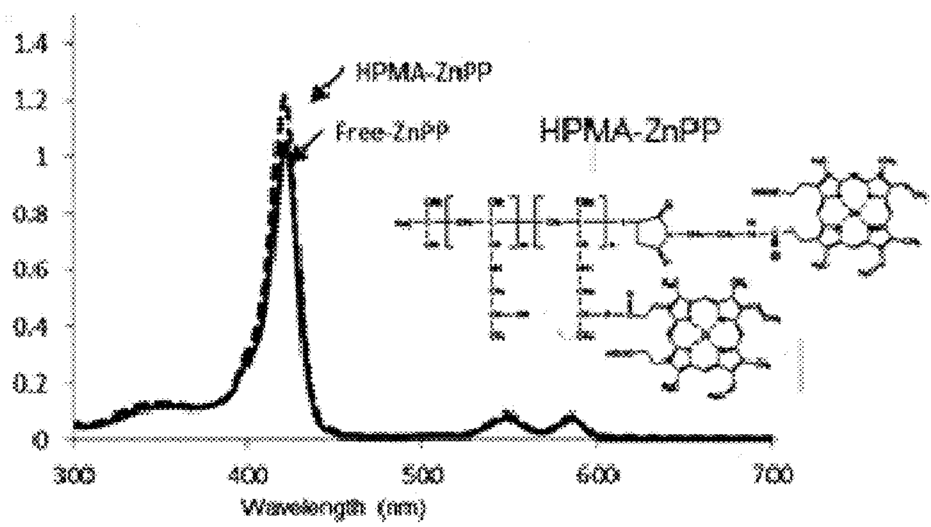
Figure 9b. UV/visible absorption spectra of HPMA-ZnPP and free ZnPP.

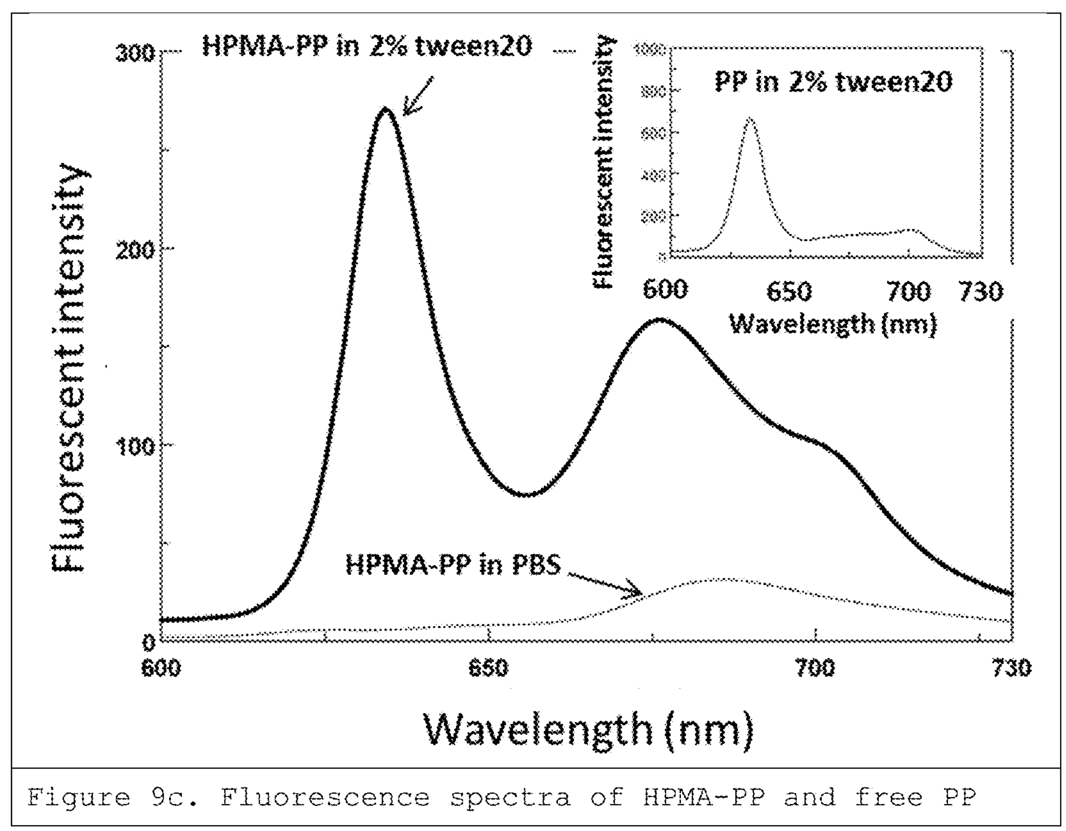
Figure 9c. Fluorescence spectra of HPMA-PP and free PP
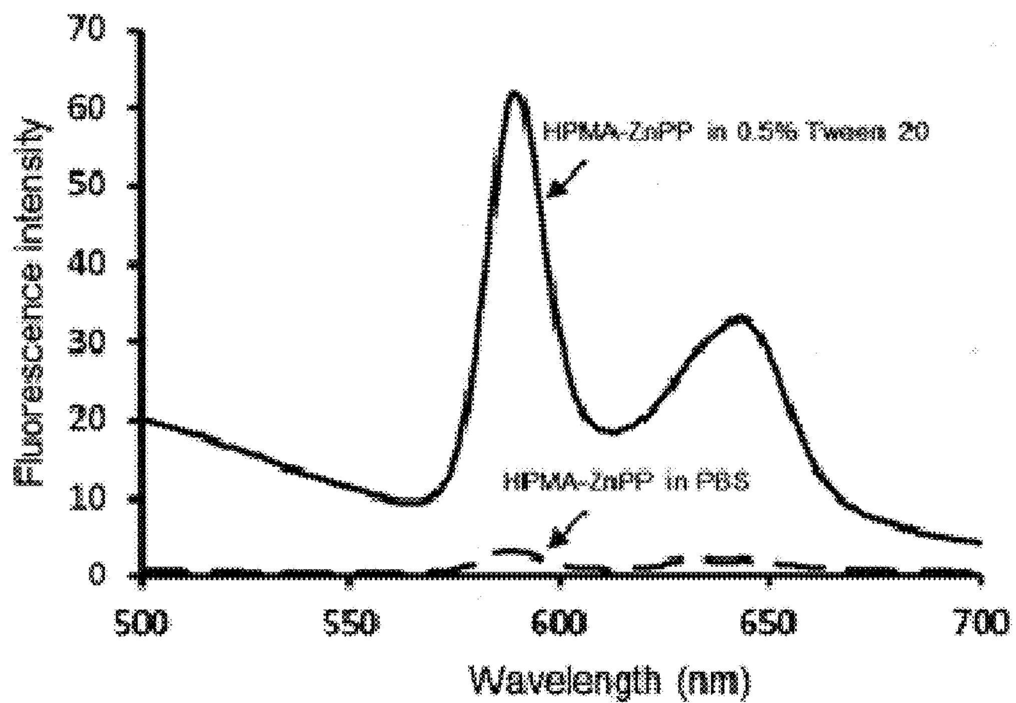
Figure 9d. Fluorescence spectra of HPMA-ZnPP and free ZnPP

[Figure 10]
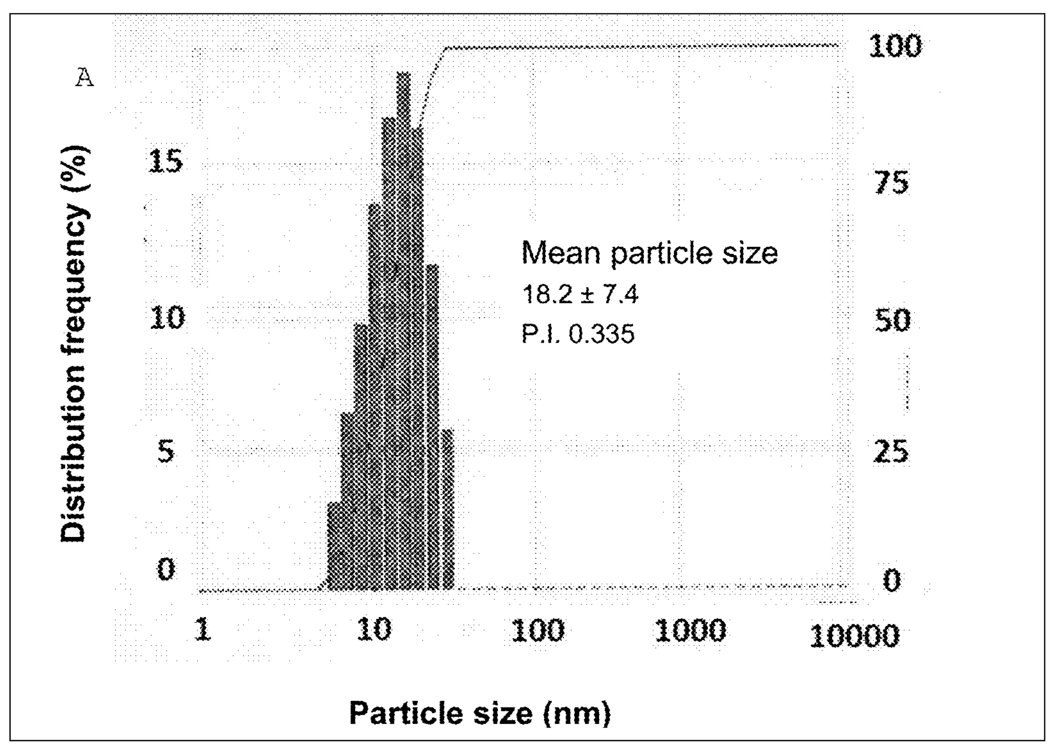
Figure 10-a. Particle size analysis of HPMA-PP.
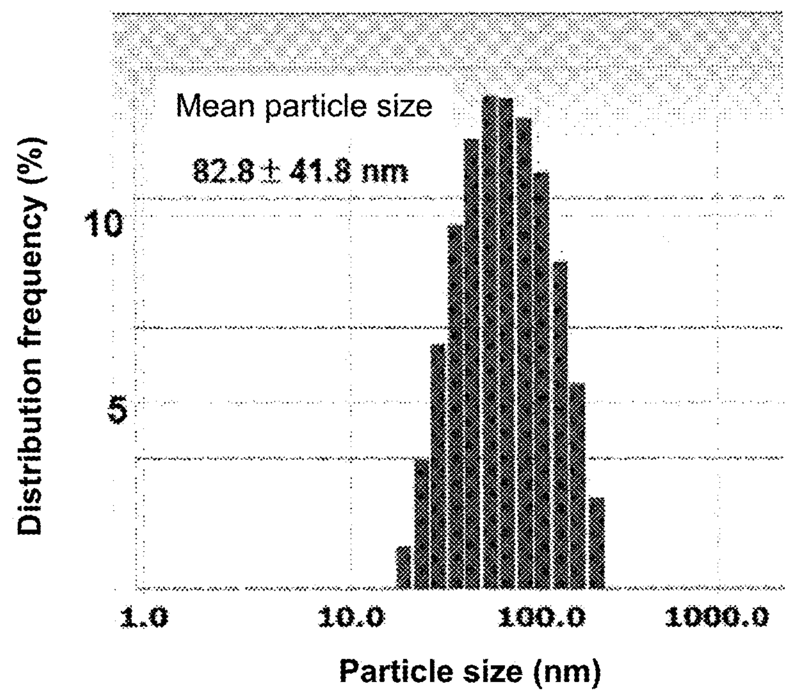
Figure 10-b. Particle size analysis of HPMA-ZnPP.

[Figure 11]
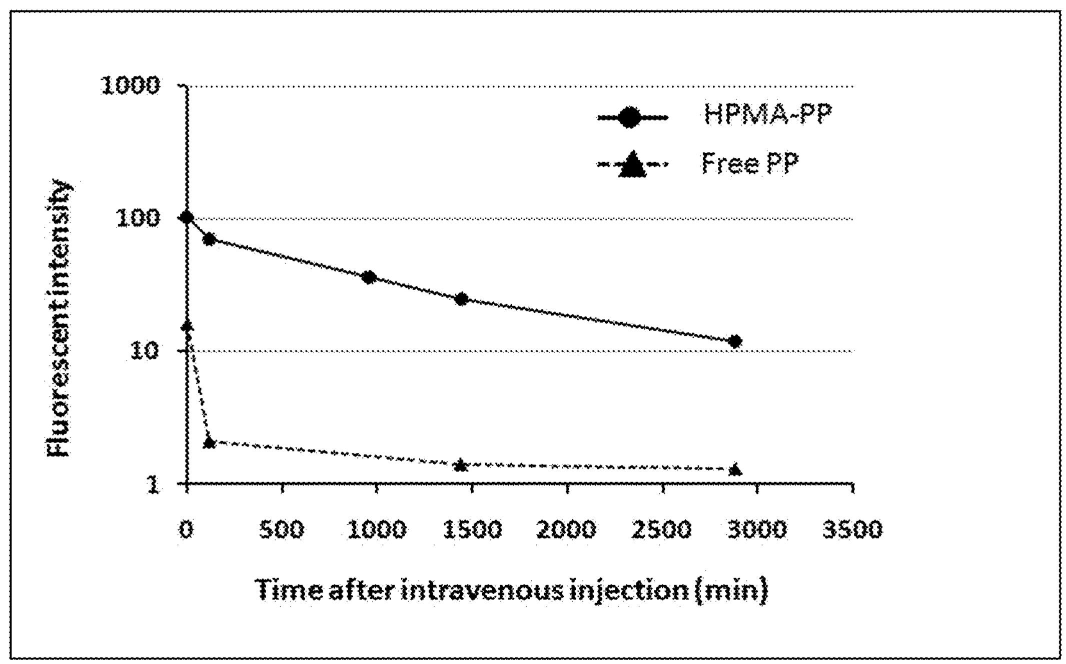
Figure 11-a. Blood kinetics of free PP and HPMA-PP
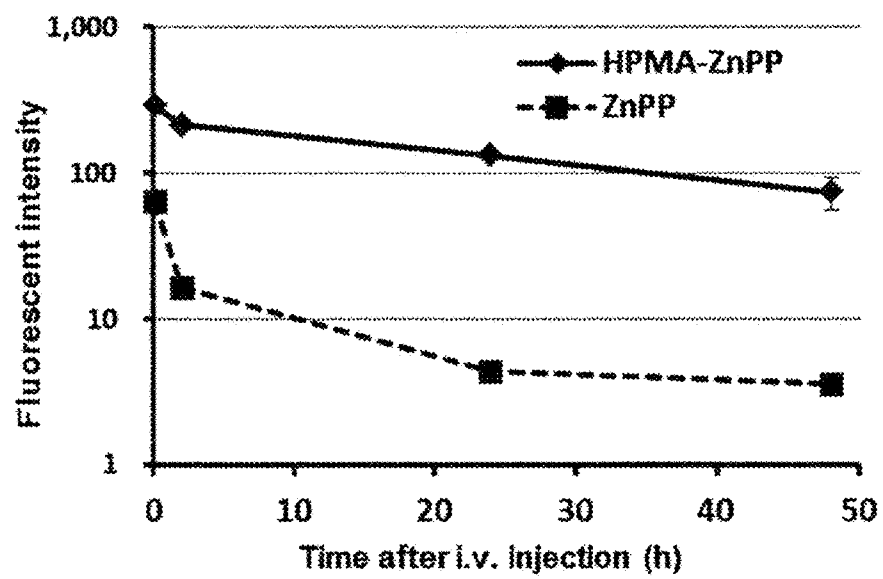
Figure 11-b. Blood kinetics of free ZnPP and HPMA-ZnPP

[Figure 12]
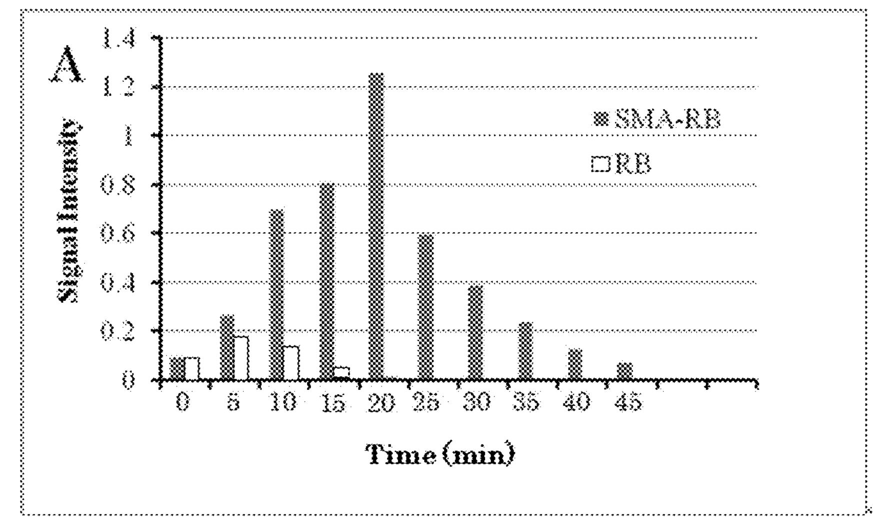
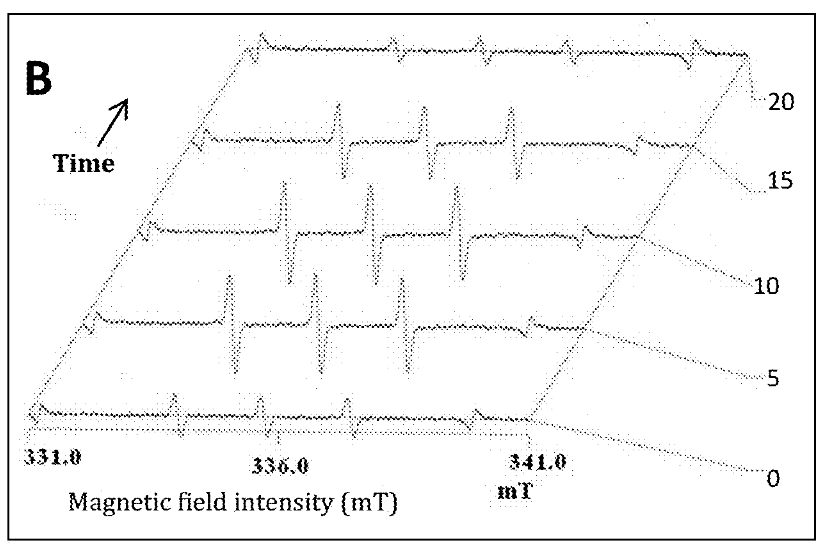
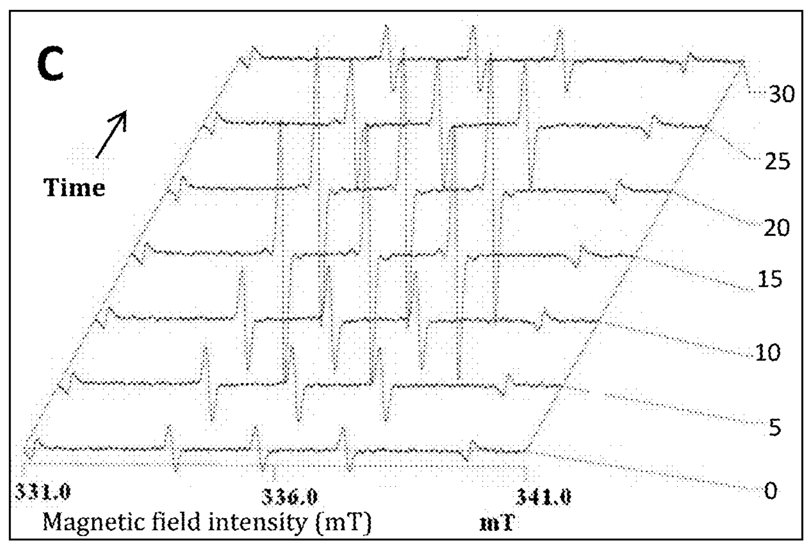

[Figure 13]
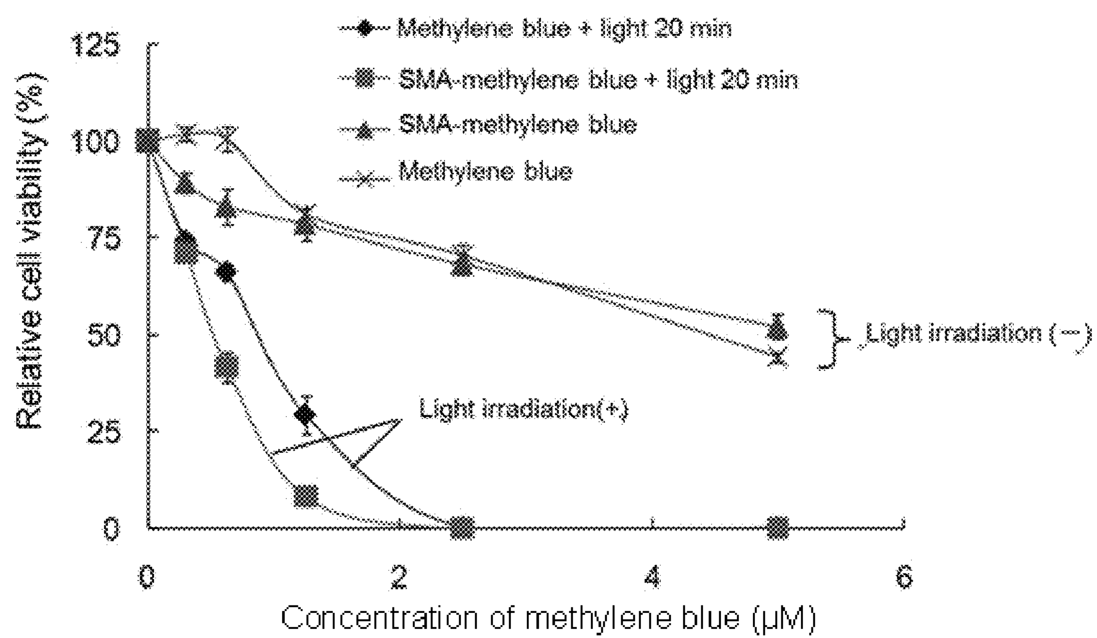

POLYMER-TYPE FLUORESCENT MOLECULE PROBE

TECHNICAL FIELD

The present application is filed claiming the priority of the Japanese Patent Application No. 2011-193237, the entire contents of which are herein incorporated by references.

The present invention relates to fluorescent molecular probes for implementing fluorescent detection (visualization) of tumors or, in addition to the fluorescent detection, photodynamic treatment, for instance, by using fluorescence endoscope or fluorescent laparoscope.

BACKGROUND ART

Cancer (tumor) is the number one disease as a cause of death in Japan. With exception of early stage gastric and cervical cancers by surgical operation, which yield fair numbers of success cases. Although a relatively good therapeutic results in lymphocytic leukemia by use of chemotherapy are known: other remaining many cancers, for instance, metastatic liver cancer, cancers of the lung, breast, pancreas, esophagus, gallbladder/cholangio, kidney, prostate, ovary, brain, as well as metastatic cancers such as pleural and abdominal carcinoma, achieved little progress in the past 30 years. (Non-patent Document 1: Fortune (2004), March issue).

Early detection at Stage 1 followed by curative surgery would yield improved therapeutic outcome as observed in gastric cancer, with exception of the liver cancer of which etiology is chronic infection of hepatitis viruses.

Under these circumstances, the present inventors have conducted research concerning the method of delivering macromolecular (or polymeric) drugs selectively to tumors, and discovered a new concept of EPR-effect (enhanced permeability and retention effect) and reported (Non-Patent Document 2: Cancer Research, 1986 (12) 46, 6787-6392). Further, the present inventors have developed and reported macromolecular cancer therapeutic agents such as SMANCS, the first macromolecular bound anticancer agent, and other macromolecular miceller anticancer drugs [Patent Document 1: WO 2004/103409; Patent Document 2: WO 2006/112361; Non-Patent Document 3: Adv. Drug Deliv. Rev. 6, 181-202 (1991); Non-Patent Document 4: J. Control. Release, 74, 47-61 (2001); and Non-Patent Document 5: Bioconj. Chem. 21, 797-802 (2010), etc.]

PRIOR ART DOCUMENTS

Patent Documents

Patent Document 1: WO 2004/103409
Patent Document 2: WO 2006/112361

Non-Patent Documents

Non-patent Document 1: Fortune 2004, March
Non-patent Document 2: Cancer Research. 1986 (12), 46, 6787-6392.
Non-patent Document 3: Adv. Drug Deliv. Rev. 6, 151-202 (1991)
Non-patent Document 4: J. Control. Release, 74, 47-61 (2001)
Non-patent Document 5: Bioconj. Chem. 21, 797-802 (2010)

SUMMARY OF INVENTION

Problem to be Solved by the Invention

The object of the present invention is to develop macromolecular fluorescent molecular probes for efficient fluorescent detection (visualization) of tumors or for implementing fluorescent detection and photodynamic treatment, for instance, by using fluorescence endoscope or fluorescent laparoscope, and a novel complex useful as said fluorescent molecular probes.

Means for Solving the Problem

The present inventors have rigorously investigated to solve the above object, and completed the present invention. Namely, the inventors have been successful to develop macromolecular fluorescent (FL) molecular probes that can fluoresce upon irradiation of a specified wavelength of light, and macromolecular fluorescent/photosensitizing (FL/PS) molecular probes that can fluoresce and generate singlet oxygen ($^1O_2$) by light irradiation.

The present invention includes the followings:

[1] A macromolecular fluorescent molecular probe for fluorescent detection of tumor comprising a complex comprising a fluorescent molecule and a biocompatible macromolecule (or polymer).

[2] The macromolecular fluorescent molecular probe according to the above [1], which is for fluorescent detection of tumor by using with a fluorescent endoscope or a fluorescent laparoscope.

[3] The macromolecular fluorescent molecular probe according to the above [1], which is used as an antitumor agent for photodynamic treatment.

[4] A complex comprising a fluorescent molecule and a biocompatible macromolecule, wherein the biocompatible macromolecule is selected from hydroxypropylmethacrylamide copolymers, hydroxypropylmethacrylamide copolymers having an introduced functional group, and mixtures thereof.

[5] A complex comprising a fluorescent molecule and a biocompatible macromolecule, wherein the fluorescent molecule is selected from rose bengal, indocyaninegreen, Zn bound phthalocyanidine, porphyrins, Zn bound pheophorbide, methylene blue, Zn bound foscan, Zn orthophenanthroline, Cu phenanthroline, acriflavine, acrinol, acridine diamine, acridine, acridine orange, tetracycline, aminofluorescein, tetramethylrhodamine, aminorhodamine, dichlorofluorescein, and mixtures thereof, and the biocompatible macromolecule selected from styrene-maleic acid copolymers, styrene-maleic acid copolymers having a multiple-functionalized maleic acid side chain, hydroxylpropylmetaacrylamide copolymer, serum albumin, transferrin, immunoglobulin, $\alpha_1$-acidglycoprotein, $\alpha_1$-antitrypsin, solubilized gelatin, polyvinylalcohol, polyvinyl pyrolidone, and mixtures thereof.

[6] The complex according to the above [4] or [5], wherein fluorescent molecule is selected from rose bengal, methylene blue, Zn bound foscun, acridine, riboflavins, chlorophyll, porphyrins, and mixtures thereof.

[7] The complex according to the above [5], wherein the biocompatible macromolecule is selected from styrene-maleic acid copolymers, styrene-maleic acid copolymers having a multiple-functionalized maleic acid side chain, and mixtures thereof.

[8] The complex according to any of the above [4] to [7], wherein the fluorescent molecule is non-covalently bound to the biocompatible macromolecule, and the complex is in the form of a micelle in which the fluorescent molecule is encapsulated in the biocompatible macromolecule.

[9] The complex according to any of the above [4] to [7], wherein the fluorescent molecule is covalently bound to the biocompatible macromolecule via a spacer.

[10] The complex according to any of the above [4] to [7], wherein the fluorescent molecule is covalently bound to the biocompatible macromolecule without a spacer.

[11] A method for producing the complex according to the above [7], which comprises:

(a) solubilizing a styrene-maleic acid copolymer (SMA) or its derivative in an alkali water with pH above 8, (b) adding a fluorescent molecule to the solution obtained in the above (a), and (c) bringing the pH of the mixture solution obtained in the above (b) to below pH 5 with an acid to precipitate a SMA-fluorescent molecule complex.

[12] A method for producing the complex according to the above [7], which comprises:

(a) binding a maleyl residue or a maleic anhydride residue of a styrene-maleic acid copolymer (SMA) or its derivative to a functional group of a spacer, which is reactive with the residue of the SMA or its derivative, and (b) binding a functional group of the spacer part of the product obtained in the above (a) to a functional group of a fluorescent molecule, which is reactive with the functional group of the spacer part.

[13] A method for producing the complex according to the above [7], which comprises:

(a) reacting a maleyl residue of a styrene-maleic acid copolymer (SMA) or its derivative with a functional group of a fluorescent molecule to bind the residue of the SMA or its derivative to the functional group of the fluorescent molecule.

Effects of the Invention

According to the present invention, it is possible to confer tumor-targeting capability to known fluorescent (FL) molecules, and thus to detect minute tumors with a few mm in diameter by fluorescence. Namely, by irradiating the fluorescent molecular probe with excitation light wavelength by using a light source of endoscope, specific detection (visualization) of tumors becomes possible. In addition, when a fluorescent molecule is a photosensitizing (PS) molecule, the molecule can generate singlet oxygen ($^1O_2$) by irradiation of an excitation light to kill tumor cells (tissue) (thus photodynamic treatment).

Accordingly, based on the present invention, by introducing irradiation light having a suitable excitation light into the body cavity via the endoscope, laparoscope, or cystoscope, it is possible to produce fluorescence at tumor area, and thus to implement highly sensitive detection and treatment of tumors at the same time.

BRIEF DESCRIPTION OF THE DRAWINGS

FIG. 1 shows a flow chart of a method for preparing a macromolecular fluorescent molecular probe of the present invention [Method I].

FIG. 2 shows a reaction scheme of a method for preparing macromolecular fluorescent molecular probes of the present invention [Method II].

FIG. 3 shows high sensitive tumor detection by using a macromolecular fluorescent molecular probe of the present invention.

FIG. 4 shows a conceptual picture of generation of fluorescence and singlet oxygen [$^1O_2$] upon disruption of micelle structure.

FIG. 5 shows spectroscopic characters (UV-visible absorption spectra (A), and Fluorescent spectra (B)) of SMA micelle encapsulating methylene blue (MB) (SMA-MB micelle).

FIG. 6 shows spectroscopic characters (UV-visible absorption spectrum (A)(a, b) and Fluorescence spectrum (B)) of SMA micelle encapsulating indocyaninegreen (ICG) (SMA-ICG micelle).

FIG. 7 shows spectroscopic characters (UV-visible absorption spectra (A) and Fluorescence spectra (B)) of SMA-micelle encapsulating rose bengal (RB).

FIG. 8 shows spectroscopic characters (UV-visible absorption spectra (A) and Fluorescence spectra (B)) of SMA-micelle encapsulating Zn-foscan.

FIG. 9 shows UV-visible absorption spectra (in DMSO) of (a) protoporphyrin (PP)-HPMA covalently bound complex (HPMA-PP) and free PP, and (b) Zn protoporphyrin (ZnPP)-HPMA covalently bound complex (HPMA-ZnPP) and free ZnPP, and fluorescence spectra (in aqueous solution) of (c) HPMA-PP and free PP. HPMA-PP exists as micelle in aqueous solution, and has little fluorescence. However, it shows fluorescence when the micelle structure is disintegrated in the presence of 2% Tween 20. (d) shows fluorescence spectra of HPMA-ZnPP. HPMA-ZnPP has little fluorescence, but it shows fluorescence when the micelle structure is disintegrated in the presence of 0.5% Tween 20.

FIG. 10 shows size distribution as revealed by dynamic light scattering of (a) HPMA-PP micelles and (b) HPMA-ZnPP micelles.

FIG. 11 shows blood kinetics of (a) free PP and HPMA-PP and (b) free ZnPP and HPMA-ZnPP. HPMA-PP or HPMA-ZnPP shows several 10-fold higher level than free PP or free ZnPP in AUC (the area under the plasma drug concentration-time curve), and thus the former is more effective than the latter.

FIG. 12 shows generation profile of singlet oxygen [$^1O_2$] by free rose bengal (RB) and a SMA-RB molecule upon light irradiation. Panel (A) shows the time-dependent change of the ESR signal upon light irradiation of free RB and SMA-RB micelles both at 33.0 μM. Panel (B) shows the ESR spectra of RB. Panel (C) shows the ESR spectra of SMA-RB micelles.

FIG. 13 shows tumor cell killing activity of SMA-MB micelle on human pancreatic cancer cells PC 1.0 cells.

DESCRIPTION OF EMBODIMENTS

The macromolecular fluorescent molecular probe of the present invention comprises a complex comprising a fluorescent (FL) molecule (hereinafter referred to as "FL molecule") and a biocompatible macromolecule (or polymer), which is capable of fluorescent detection (or visualization) of tumors using a fluorescence endoscope or a fluorescent laparoscope. Further, when the FL-molecule is also a photosensitizing molecule (hereinafter referred to as "FL/PS molecule") that can generate singlet oxygen [$^1O_2$] under light irradiation, it is useful for implementing photodynamic treatment in addition to fluorescent detection of tumor.

The above fluorescence (FL) molecule can emit fluorescence light upon irradiation of specific wavelength light, and includes, for instance, rose bengal, indocyanin green (ICG), Zn bound phthalocyanine, porphyrins, Zn bound pheophorbide, methylene blue, Zn bound foscan, Zn-orthophenanthroline, Cu phenanthrorin, acriflavine, acrinol, acridine amine, acridine, acridine orange, tetracycline, aminofluorescein, tetramethylrhodamine, aminorhodamine, dichlorofluorescein, Zn bound protoporphyrin (ZnPP), aclarubicin, doxorubicin, pirarubicin, and the like. Among them, preferred are rose bengal, indocyaningreen (ICG), methylene blue, Zn bound foscan, Zn bound protoporphyrin, and tetramethylrhodamine.

Among the above FL molecules, preferred are photosensitizing (PS) molecules (FL/PS molecules) which can generate singlet oxygen, a type of reactive oxygen species, upon light irradiation. Examples of the FL/PS molecule include rose bengal, methylene blue, Zn bound foscan, Zn bound protoporphyrin (ZnPP), aclarubicin, doxorubicin, pirarubicin, and the like. Among them, preferred are rose bengal, methylene blue, Zn bound foscan, and Zn bound protoporphyrin.

In the present invention, FL molecules (including FL/PS molecules) can be used alone or in a mixture thereof.

The above biocompatible macromolecule refers to a macromolecule which has no antigenicity and no immunogenicity, does not induce allergy, shock, and the like, does not effect on blood coagulation and complement activation, does not accumulate in the body for a long time, and is non-toxic, and is useful for converting the FL molecule to a macromolecule (having a molecular weight of not less than several ten thousands) which is capable of achieving a high intra tumor concentration by virtue of the EPR effect thereof. Examples of the biocompatible macromolecule include styrene-maleic acid copolymers (SMA), SMA having a multiple-functionalized maleic acid side chain, hydroxypropylmethacrylamide (HPMA) polymers, and HPMA having an introduced functional group, serum albumin, transferrin, immunoglobulin, $\alpha_1$-acid glycoprotein, $\alpha_1$-antitrypsin, polyethylene glycol, polyvinyl alcohol, chitin/chitosan, polyvinylpyrrolidone, soluble gelatin, polyaminoacids (e.g., polyaspartic acid) and the like. Among them, preferred are SMA, SMA having a multiple-functionalized maleic acid side chain, HPMA, HPMA having an introduced functional group, and serum albumin.

In the present invention, the biocompatible macromolecule can be used alone or in a mixture thereof. When a mixture of two or more biocompatible macromolecules is used, all of the biocompatible macromolecules are not necessarily conjugated to the FL molecule, and only specific biocompatible macromolecule may be conjugated to the FL molecules. Further, two biocompatible macromolecules may be connected to each other (for instance, as described later, SMA-albumin, SMA-transferrin, HPMA-albumin, HPMA-transferrin, and the like).

The styrene-maleic acid copolymer (SMA) is a copolymer generally comprising a repeating unit as shown in the formula (1) below, and comprises a styrene unit and a maleic acid (or maleic anhydride) unit as essential component unit. SMA may be obtained in the market, or synthesized by known synthesis procedure. It is generally obtained by copolymerization of styrene and maleic anhydride. In this case, the residue from maleic anhydride in SMA will be an anhydride, this can be used as is, or as free carboxyl form by hydrolysis before use.

[Formula 1]

(1)

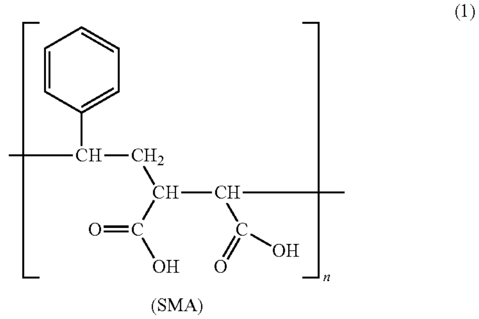

(SMA)

Examples of the “SMA having a multiple-functionalized maleic acid side chain” described above may be those having a maleic acid side chain to which albumin or transferrin is conjugated; those having a maleic acid side chain of which the carboxyl group is alkylated such as ethylated, butylated, modified with butyl cellosolve, or the like; those having a maleic acid side chain of which the carboxyl group is amidated, aminoethylated, trishydroxyaminoethylated, hydroxyaminomethanized, mercaptoethylaminated, polyethylene-glycolated (PEG), or amino acidified (e.g., lysine, cysteine, other amino acid conjugates, and the like); and those having a maleic acid side chain modified with hydrazine.

The SMA having a maleic acid side chain to which albumin or transferrin is conjugated includes SMA-albumin, and SMA transferrin.

The SMA having a maleic acid side chain of which the carboxyl group is butylated or modified with butyl cellosolve includes SMA Resins® (Sartomer Inc., USA).

The above hydroxypropylmetaacrylamide (HPMA) polymer comprises a repeating unit shown in brackets [ ] of formula (2) below. HPMA has excellent biocompatibility and is devoid of immunogenicity or inflammation-inducing capacity, and hence it may be advantageously used as a component of the complex of present invention.

The HPMA to be used in the present invention may be obtained from commercial sources or may be synthesized by the known method. In general it may be synthesized by standard radical polymerization using hydroxypropylacrylamide monomer in dimethylacetoamide as solvent using AIBN (2,2'-azobis-isobutylonitrile) as a initiator of the polymerization reaction at 70° C. for instance.

[Formula 2]

(2)

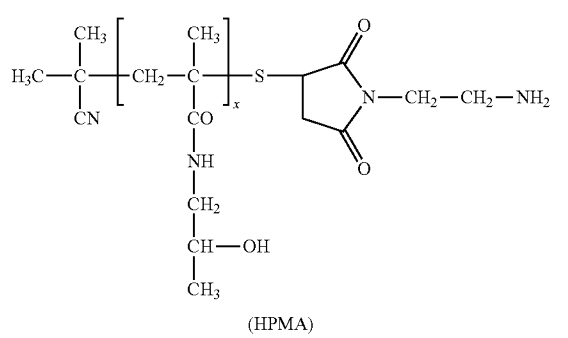

(HPMA)

-continued

[Formula 3]

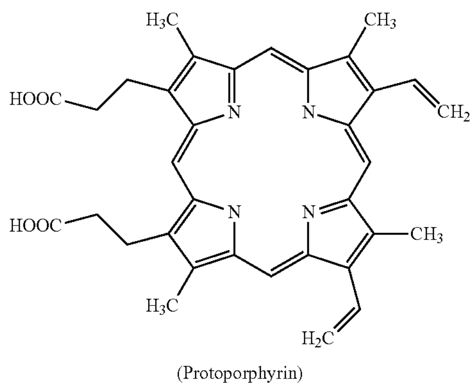

(Protoporphyrin)

Examples of "HPMA having an introduced functional group" include those having a group with a terminal amino group as shown in the above formula (2); derivatives thereof to which carboxyl group, any of amino acids or peptides, or hydrazine is introduced; derivatives thereof amidated, ethylaminated, mercaptoethylaminated, or trishydroxymethanized; and the like.

These derivatives of HPMA may be prepared, for example, in water or in a solvent in similar manner as in conventional peptide synthesis. For instance, the derivative represented by the above formula (2) may be conjugated to FL molecule or FL/PS molecule either via a terminal amino group or a hydroxyl group of hydroxypropyl group. For example, when FL molecule or FL/PS molecule is protoporphyrin [see formula 3 above], either or both of two carboxyl residues of protoporphyrin may be reacted with hydroxyl group(s) of HPMA by using a conventional dehydration/condensation agent for forming an amide or ester bond to give a desired conjugate (cf. FIG. 9*a*, the bond of the inset formula HPMA-PP therein is an ester bond). The number of PP to be conjugated to HPMA is not particularly limited.

The above HPMA derivative having a terminal amino group represented by the formula (2) can be conjugated to albumin or transferrin via amide bond formed from the amino group of the derivative and the carboxyl group of albumin or transferrin to give a conjugate such as HPMA-albumin, HPMA-transferrin, and the like. Such conjugates can be used to form complexes with fluorescent (FL) molecules in the present invention.

Depending upon the degree of polymerization, varieties of SMA or HPMA with different molecular weight may be available. However, SMA to be used in the present invention may be preferably its trimmer (about 660 Da) to those having a molecular weight of about 40 KDa, most preferably between 800 to 2500. As to HPMA, preferred are those having a molecular weight of between 1000 to 20000.

The above complexes comprising fluorescent (FL) molecules and the biocompatible macromolecule may be produced by, for instance, [Method I] to [Method III] below. Depending on the production methods, the complexes are classified into those wherein the FL molecule is covalently bound to the biocompatible macromolecule, and those wherein the FL molecules are non-covalently bound to the biocompatible macromolecules and they formed a micelle. Also, the complexes comprising the FL molecule covalently bound to the biocompatible macromolecule may aggregate to form a micelle (e.g., see FIG. 9*b*).

[Method I] Styrene-Maleic Acid Copolymer [SMA] Micelle of FL Molecules

Method I is to encapsulate the FL molecules in a SMA micelle. In this case, FL molecules are not covalently bound to SMA. This micelle may be prepared according to the flow chart shown in FIG. 1.

Namely, SMA, if it contains maleic anhydride parts, in intact form as is, or after hydrolysis of the maleic anhydride parts or modification such as alkyl esterification of the parts as needed, is solubilized by adding an aqueous alkaline solution (i.e., water containing an alkali such as 0.1M NaOH aqueous solution) to bring its pH to pH above 8 (e.g., pH around 8.5). To this solution is added FL molecule to react with SMA. This mixing step is preferably carried out under stirring.

In this system, the ratio (w/w) of SMA to FL molecule is not particularly limited as long as the FL molecule can be capsulated in a micelle, but, for instance, the FL molecule may be 1 to 80 parts (w/w) relative to 100 parts of SMA. The temperature and time in the mixing (stirring) step of SMA and the FL molecule are not particularly limited, but, for example, the temperature may be around room temperature (25° C.) and the time may be 1 to 2 hours.

Then, the mixture is acidified by adding an acid (e.g., 0.1M HCl) to bring its pH to below pH 5 (e.g., pH about 4.8). As a result, precipitates may be formed. The precipitates thus formed may be collected by centrifugation (e.g., at 5000 rpm), and the supernatant may be discarded. Thus, FL molecule-SMA (micelle) complex may be obtained.

The obtained complex (ppt) may be further subjected to purification, if necessary. Purification methods are not particularly limited and may be carried out by known methods. For instance, the complex (ppt) may be purified by repeating the following procedures: dissolution in an aqueous alkaline solution at pH 7 to 8, followed by dialysis, ultrafiltration, and concentration. In addition, the complex after purification may be lyophilized.

Followings are more detailed procedures of Method I.

At first, 100 mg of SMA copolymer (or its alkyl ester half butylated derivative, etc.) is weighted and placed in 200 ml beaker, and 30 to 60 ml of distilled water is added thereto, and while monitoring the pH with pH meter, slowly added is 0.1M NaOH under stirring and bring up the pH to pH about 8.5. Next, to the mixture is added 30 mg in total of a powder of methylene blue at 5 to 10 mg aliquot at a time under stirring. After stirring the mixture for additional 1 to 2 hours at room temperature, to the mixture is add 0.1M HCl slowly to bring its pH to pH 4.8 or below to give SMA micelle form of methylene blue as precipitate. As all SMA-methylene blue micelle is precipitated, the solution is further centrifuged (5000 rpm) to collect precipitates. Then, the precipitates are suspended by adding 60 ml of 1 mM HCl at ice-cooled condition and washed by centrifugation (5,000 rpm) to collect the precipitates. The precipitates are dispersed into 300 ml of distilled water, and the pH of this dispersion is brought to about neutral by adding dropwise 0.1M NaOH to solubilize the precipitate completely. This solution is subjected to the molecular filtering system, Lab Scale TFF system (Millipore Ltd.) having cut off molecular size of 10 KDa, and filtered/concentrated to 30 ml under reduced pressure. Then, to the concentrate is added 400 ml of distilled water, followed by dialysis/concentration procedure to 40 ml twice, and then the concentrate is lyophilized to obtain 90 to 100 mg of blue powder.

In the above procedures, foscan, indocyaningreen, rose bengal, or other fluorescent molecules can be used in place of methylene blue in the macromolecular miceller encapsulation.

[Method II] Production of Complex Comprising Fluorescent Molecule and SMA Wherein the Fluorescent Molecule is Covalently Bound to SMA.

Method II is to bind the maleyl residue of SMA to the fluorescent molecule via a spacer. Namely, this method is to bind SMA to the fluorescent molecule covalently.

The above spacer is not particularly limited as long as it has a functional group (e.g., amino group, carboxyl group, hydroxyl group, and the like) that is reactive to maleic acid residue or maleic anhydride residue, and at the same time, a functional group (e.g., amino group, hydroxyl group, and the like) that is reactive to a functional group of the fluorescent molecule, but includes ethylenediamine, lysine, cysteine, ε-amino caproic acid, and the like.

The amount (molar ratio) of the spacer to be used is 0.1 to 1.0 mol relative to 1 mol of the maleic anhydride residues which exist two or more in SMA.

In the above method, at first, the maleic acid residue or maleic anhydride residue of SMA is conjugated to a functional group of the spacer, which is reactive to these residues (step (a)). Here, the temperature and time are not particularly limited, but, for example, the temperature may be around room temperature (25° C.) and the time may be overnight.

Then, a functional group of the spacer part of the resultant product in the above step (a) is conjugated to a functional group of the fluorescent molecule, which is reactive to the functional group of the spacer part (step (b)). The temperature and time are not particularly limited, but, for example, the temperature may be 0° C. to 80° C., preferably at 4° C. to 30° C. and the time may be 1 to 300 hours. The pH in the step (b) may vary depending on SMA, fluorescent molecule and spacer to be used, but may be, for example, 8.5 to 9.0.

Followings are more detailed procedures of Method II.

As an example, a method using L-lysine as a spacer and labeling with FITC is shown (FIG. 2). In place of lysine, it is possible to use L-arginine, L-histidine, diaminoethane, ε-aminocaproic acid, or the like.

L-lysine (Lys) HCl, 100 mg, is dissolved in 50 ml of 0.1M $NaHCO_3$. Then, to the solution is added a SMA copolymer containing maleic anhydride residue under stirring and continued this coupling reaction overnight. Then, the resultant product is purified by Sephadex G-50 chromatography to separate unreacted L-lysine from SMA-lysine (Lysylated SMA) and recover SMA-Lys fraction. Eluted product is monitored by OD (optical density) at 230-260 nm (absorption). This reaction can be also carried out in a solvent such as tetrahydrofuran, dimethylformamide, and dimethylsulfoxide.

Next, the lyophilized SMA-Lys (100 mg) is dissolved in 50 ml of 0.1M $NaHCO_3$ aqueous solution while keeping the solution at pH 8.5 to 9.0. Then, to the mixture is added 20 mg of FITC to react in a similar manner to the above reaction to obtain FITC-labeled SMA.

In this procedure, rhodamine isothiocyanate (RITC) can be used in place of FITC to yield SMA-rhodamine complex.

[Method III] Preparation of Complex Comprising Fluorescent Molecule and Biocompatible Macromolecule (HPMA) Wherein the Fluorescent Molecule is Covalently Bound Directly to the Biocompatible Macromolecule.

Method III is to bind a fluorescent dye or a photosensitizer to hydroxypropyl methacrylamide polymer (HPMA) or alike by chemically reacting a functional group in a fluorescent dye or a photosensitizer, such as amino group, hydroxyl group, ketone group, or the like, with amino group (see formula (2) above), hydroxyl group, carboxyl group, cysteine group, hydrazine group, or the like in HPMA or a derivative. In this reaction, the weight ratio of biocompatible macromolecule to fluorescent molecule is not particularly limited. The reaction temperature and reaction time are not particularly limited, but the reaction may be carried out, for example, at about 30° C. for 5-20 hours.

Following are more detailed explanation of Method III.

A fluorescent dye or photosensitizer such as protoporphyrin IX (281 mg) is dissolved in DMSO, and under stirring added to this is HPMA (570 mg). To this reaction mixture, triethylamine (1 g), dimethylaminopyridine (DMAP) (1.2 g), and water soluble carbodiimide (WSC, 1-ethyl-3-(3-dimethylaminopropyl)carbodiimide) (1.92 g) are added, and reacted at 50° C. In place of WSC, DCC (dicyclohexylcarbodiimide) can be used and the reaction may be carried out in a solvent. The reaction may be performed for about 12 hours. Then to remove catalysts, small aliquot of diethyl ether is added to recover the precipitate. By repeating this process three times, protoporphyrin conjugated HPMA (HPMA-PP) is obtained as precipitate. The precipitate is dissolved in dimethylformamide, followed by gel permeation column (BioBeads S-X1) chromatography to remove unreacted PP. Subsequently, HPMA-PP is dissolved in distilled water, followed by ultrafiltration or Sephadex G-25 or G-50 column chromatography (column size: 01.0 to 5.0 cm×L 30 cm to 1.5 m) with distillated water as eluant. Then, the eluted material is lyophilized to yield powder.

[Method IV] Preparation of Complex Comprising Fluorescent Molecule and Biocompatible Macromolecule (Protein) Wherein the Fluorescent Molecule is Covalently Bound Directly to the Protein.

Method IV is to bind FL and the like to a protein and the like by chemically reacting a functional (reactive) group in FL, such as isothiocyanate (—NCS) group in fluorescent dye such as fluorescein isothiocyanate (FITC), tetramethylrhodamine isothiocyanate (TRITC), and the like, with amino group in a protein, for example, serum proteins such as serum albumin, transferrin, immunoglobulin (IgG), and the like.

In this case, the weight ratio of the biocompatible macromolecule and the fluorescent molecule is not particularly limited at specific ratio, however, as an example, 100 parts by weight of the biocompatible macromolecule to 0.5 to 10 parts by weight of the fluorescent molecule can be used. The reaction condition is not particularly limited, but, for instance, may be at about room temperature (25° C.) for about 5 to 6 hours and up to about 20 hours, and the pH in the reaction of the biocompatible macromolecule and the fluorescent molecule may be between 7 to 10, preferably about 8.5.

More detailed explanation of Method IV is described below.

Human serum albumin (100 mg) is dissolved in 0.1M $NaHCO_3$, and the pH is adjusted to 8.0 to 9.0 under stirring by a magnetic stirrer. To this solution is added a fluorescent reagent (20 mg) such as a fluorescent dye, tetramethylrhodamine isothiocyanate (TRITC), and the reaction may continue for 5 to 6 hours, for more extensive fluorescent labeling, at pH>8.5 for 20 hours. After that, the reaction mixture is dialyzed against distilled water, or applied to Sephadex G-25 or G-50 column (column size: Φ1.0 to 5.0 cm×L 30 cm to 1.5 m) chromatography using water as an eluant to remove decomposed products and unreacted reagents. The fluorescent labeled protein desalted by using dialysis tube and fluid inside; or by using Sephadex column is collected by a fraction collector, and they are subjected to lyophilization to obtain a desired complex.

Among the above complexes comprising of the fluorescent (FL) molecules and the biocompatible macromolecules, no such complex is known where the biocompatible macromolecule is selected from HPMAs, those with functional groups, and mixtures thereof.

Further, among the above complexes, the followings have not been known: those wherein the FL molecule is selected from rose bengal, indocyanine green (ICG), Zn bound phthalocyanine, porphyrins, Zn bound pheophorbide, methylene blue, Zn foscan (Foscan), Zn orthophenanthroline, Cu phenanthroline, acriflavine, acrinol, acridine diamine, acridine, acridine orange, tetracycline, aminofluorescein, tetramethylrhodamine, aminorhodamine, dichlorofluorescein (preferably rose bengal, indocyanine green (ICG), methylene blue, Zn foscan, tetramethylrhodamine), and mixtures thereof, and the biocompatible macromolecule is selected from styrene-maleyl copolymers (SMA)s, and SMAs having a multiple-functionalized maleic acid side chain, hydroxylpropylmetaacrylamide copolymers (HPMA) s, HPMAs with functional groups, serum albumin, transferrin, immune globulin, $\alpha_1$-acidglycoprotein, $\alpha_1$-antitrypsin (preferably, SMAs, SMAs having a multiple-functionalized maleic acid side chain, HPMAs, HPMAs with functional groups, and serum albumin), and mixture thereof.

The macromolecular fluorescent molecular probes of the present invention may be administered intravenously, or tumor feeding artery, or given orally as oily formulations. After administration, the fluorescent molecular probes will accumulate in the tumor and stain the tumor, and thus ductal or intracavitary tumors may be detected under a fluorescence endoscope. Also, peritoneal and pleural carcinomatosis, or peritoneal and pleural metastatic cancers or their daughter nodules, for instance, metastasis to chest wall/pleura, greater omentum, or diaphragm may be detected under a fluorescence laparoscope.

The above mentioned "fluorescence endoscope" should have matching spectroscopic properties of FL and PS to the optical system. For instance, one can install the matching filter to the fiber optics of Fuji Film, or Olympus Co. Ltd. Alternatively, an external light source such as Asahi Spectra Max303 (Asahi Spectra Ltd., Tokyo) may be also used.

The above mentioned "fluorescent laparoscope" is not particularly limited as long as it has matching spectroscopic properties as above, but includes, for instance, laparoscope of SK-2D10D or SK-2D05S of Shinko Optical Co., Ltd.

The macromolecular type fluorescent molecular probe of the present invention will have a micellar structure, and will be taken up into cancer cells more preferably by so called endocytosis, then undergo disintegration in the cell, thereby free FL will be released in the cell. Those FL are now free molecules, and if they are PS molecules, they will generate singlet oxygen upon irradiation, and exert cytotoxic effect to tumor cells.

The "photodynamic treatment" used herein refers to a method for the treatment of cancer, which can be carried out by light irradiation by using mostly an endoscopic light source for cancers in ductal organs, or by using a projector having xenon light or using a light source from Asahi Spectra for cancers on body surface, from several hours to 2 days after the administration of a macromolecular agent containing PS.

Conventional photosensitizing (PS) molecular probes used in the photodynamic treatment will be distributed throughout the whole body including tumors. This is a big problem. Especially, the photosensitivity due to the distribution of the probes to the body surface such as the skin causes a serious side effect, which result in the damage on the body surface tissue (cells) even ambient light of indoor or outside the house. The inventors have made successful conversion of low molecular weight PS molecule to macromolecule, thereby providing the selective accumulation of the PS macromolecule in the tumor. This means its accumulation to normal skin is avoided and little chance of photosensitivity would occur. Furthermore, since the PS macromolecules accumulate in tumors much higher than normal tissues, visualization of minute tumor nodules by fluorescence become possible, and then therapeutic effect even with relatively low input of light irradiation will permit efficient generation of singlet oxygen in the tumor selectively, which is otherwise impossible with low MW PS molecules. It is expected that damages such as breakage of nervous systems or blood vessels caused by high-energy laser may be avoided and tumors located relatively deep tissues may be effectively treated.

Indocyaninegreen (ICG) and rose bengal described herein as photosensitizing (PS) molecule are known to bind to serum albumin after intravenous injection. This conjugate (complex) may be separated into free albumin and the PS molecule in the liver, and then the PS molecule is excreted into the bile efficiently. In healthy man the half-life of the PS molecule in the blood is 15 to 30 min. This relatively short residence time in blood is not enough to show the EPR effect. In contrast, SMA micelle encapsulating rose bengal, SMA micelle containing ICG, or the like in the present invention may have a half-life of 500 min or longer, and exhibit a time dependent tumor uptake phenomenon, EPR effect, to show significantly higher accumulation in tumors [FIG. 3].

Singlet oxygen has a very high reactivity and hence it can travel to a distance of only 0.1 μm in biological system. This indicates that the uptake into the target cells of the PS molecule producing singlet oxygen is necessary for providing the cytopathy of singlet oxygen. When the fluorescent/photosensitizing (FL/PS) molecules are accumulated in tumor tissues, but not uptake in the tumor cells, the FL/PS molecules can be used for the visualization of tumor tissues by fluorescence, but not efficiently used as photosensitizing agent. The conversion to polymer carrier by SMA micellar formulation have the advantage of being able to enhance the uptake of FL/PS probes in cells. Regarding the conversion to macromolecular nature of FL/PS probes other than micellar formation, the conjugate of FL/PS to albumin, transferrin, IgG or the like can be conjugated to SMA to facilitate their internalization into tumor cells.

There may be another big problem of non-specific fluorescence in non-tumorous tissue during the fluorescent tumor detection. The advantage of macromolecular fluorescent molecular probes is that the probes are minimally distributed in the normal tissue due to the EPR effect. For attaining the EPR effect, the plasma circulation time of such FL/PS probes need to be long enough. Circulating FL/PS probes may be fluorescent as background in the normal tissue, and thus tumor tissue fluorescence may be not high and poor S/N ratio is obtained. This problem may be, however, solved by micellar formation with SMA. When such FL/PS molecules are compactly folded in the SMA micelles, they do not fluoresce. Thus, no generation of singlet oxygen ($^1O_2$) will be seen when the PS molecules are packed in SMA micelles. Namely, fluorescence by light illumination is not seen when the FL/PS molecules are packed in micelles in blood. Once SMA micelles encompassing FL/PS molecules are arrived at tumor cells by the EPR effect and taken up into the cells, the SMA micelles will be disintegrated and release free FL/PS molecules. By illumination of light in excitation wavelength region, free FL/PS molecules can fluoresce and generate $^1O_2$ (singlet oxygen). Accordingly, probes packed in SMA micelles in blood do not fluoresce and generate singlet oxygen ($^1O_2$) even though they are illuminated by light (see FIG. 4). Since the probes are not fluorescent in normal tissues or blood vessels and no non-specific fluorescence and no generation of $^1O_2$ are seen in normal tissues, the tumor visualization detection by tumor-specific fluorescence and the tumor selective generation of $^1O_2$ become possible.

The complexes of the present invention may be used for photodynamic treatment (PDT). The light source to be used for PDT may be He/Ne laser, xenon lamp and the like. Because the FL molecules to be used for the present invention is adaptable to a wide range of excitation wavelength for fluorescence, it is preferable to use xenon lamp light source rather than laser light source, which can emit only at a given wavelength.

For the effective detection of the macromolecular fluorescent molecular probe of the present invention, it is possible to use endoscope, laparoscope, cystoscope, or the like, equipped with CCD camera, an excitation light filter and a fluorescence light filter, wherein the filters are adapted to the properties of the fluorescent molecular probe.

EXAMPLES

<Example 1> Preparation of SMA Micelle Encapsulating Methylene Blue (MB), i.e. SMA-MB Micelle Firstly, 100 mg of SMA copolymer (product of Sartomer, USA; or its alkyl ester half butylated derivative, etc.) was weighted and placed in 200 ml beaker, and added to this was 30 to 60 ml of distilled water. While monitoring the pH with a pH meter, 0.1M NaOH was slowly added thereto under stirring and the pH was brought to about 8.5. Then, to 10 mg of methylene blue (MB, Wako Pure Chemical Industries, Ltd., Osaka) powder was added thereto several aliquots up to a total of 30 mg. After 1 to 2 hours of mixing, added to this was 0.1M HCl to lower the pH to about 4.8 until blue precipitates appeared. After centrifugation (5000 rpm) of this suspension, precipitates were collected. Then, the precipitates were suspended and washed with 60 ml of ice cold 1 mM HCl. By further centrifugation at 5000 rpm, the resultant precipitates were collected. Then, the precipitates were suspended in 300 ml of distilled water and added dropwise to this was 0.1M NaOH to bring the suspension to a complete solution at about neutral pH. This solution was subjected to Milipore Labscale TPF system for concentration and dialysis which is equipped with cut-off membrane of MW 10 KDa, and concentrated to 30 ml under positive pressure. To this was added 400 ml of distilled water, and the mixture was dialyzed and concentrated to 40 ml. The procedure was repeated twice. The concentrated product was lyophilized to yield 90 to 100 mg of blue powder.

The UV-visible absorption and fluorescence spectra are shown in FIG. 5.

<Example 2> Preparation of SMA Micelle Encapsulating ICG (Indocyanine Green), i.e. SMA-ICG Micelle SMA-ICG micelle (yield: about 10 mg) was obtained a similar manner to Example 1 except that indocyanine green (ICG) was used instead of methylene blue. The absorption and fluorescence spectra are shown in FIG. 6.

<Example 3> Preparation of SMA-Micelle Encapsulating Rose Bengal (RB), i.e. SMA-RB Micelle SMA-RB micelle (yield: about 100 mg) was obtained similar manner to Example 1 except that indocyanine, rose bengal (RB) was used instead of methylene blue. The UV-visible absorption and fluorescence spectra are shown in FIG. 7.

<Example 4> Preparation of SMA Micelle Encapsulating Zn-Foscan, i.e. SMA-Zn-Foscan Micelle SMA-Zn-foscan micelle (yield: about 90 mg) was obtained in a similar manner to Example 1 except that Zn-foscan was used instead of methylene blue. The UV-visible absorption and fluorescence spectra are shown in FIG. 8.

<Example 5> Preparation of Protoporphyrin Conjugated HPMA (HPMA-PP) and Zn-Protoporphyrin (ZnPP)-HPMA Covalently Bound Complex (HPMA-ZnPP Protoporphyrin IX (281 mg) was dissolved in DMSO, and a powder of HPMA copolymer (570 mg) was added under stirring with magnetic stirrer. Added to this were tetraethylamine (1.0 g), DMAP (1.2 g) and WSC (1.92 g), and allowed to react at 50° C. under stirring. Then, the reaction was continued for about 12 hours. In the next step, to remove the catalysts, diethylether was added and the precipitates were recovered. This step was repeated three times to obtain protoporphyrin conjugated HPMA (HPMA-PP) as precipitates. Then, HPMA-PP was dissolved in dimethylformamide and subjected to gel permeation chromatography column (BioBeads S-X1) to remove unreacted PP. After that, HPMA-PP was dissolved in distilled water, followed by dialysis using 10 KDa dialysis membrane or chromatography using Sephadex G-25 or G-50 column (column Φ: 1.0 to 5.0 cm×L 30 cm to 1.5 m) with water as an eluant. Then, the resultant solution was lyophilized to obtain a powder (yield: about 650 mg). The UV-visible absorption and fluorescence spectra are shown in FIGS. 9*a* and 9*c*, respectively.

HPMA-ZnPP (yield: about 630 mg) was obtained in a similar manner to the above except that 280 mg of Zn-protoporphyrin (ZnPP) was used instead of protoporphyrin IX. The UV-visible absorption and fluorescence spectra are shown in FIGS. 9*b* and 9*d*, respectively.

<Particle Size Distribution of HPMA-PP and HPMA-ZnPP>

HPMA-PP or HPMA-ZnPP obtained above was dissolved in physiological saline at a concentration of 1 mg/mL, and a particle size analyzer (Photal Model ELSZ2, Ohtsuka Electron Inc., Osaka, Japan) was used to measure the size distribution of HPMA-PP or HPMA-ZnPP. The size distributions of HPMA-PP and HPMA-ZnPP are shown in FIGS. 10*a* and 10*b*, respectively. As a result, the mean diameter of HPMA-PP was 18.2±7.4 nm, and the mean diameter of HPMA-ZnPP was 82.8±41.8 nm.

<Behavior of HPMA-PP in Circulating Blood>

HPMA-PP was dissolved in physiological saline and the solution was injected at the dose of 30 mg/kg via the tail vein of ddY mice. Under ether anesthesia, blood was taken after laparotomized mice from the inferior vena cava with heparinized syringe at 5 min, 2 hours, 24 hours, and 48 hours after iv injection of HPMA-PP. After centrifugation of the blood samples, at 2000 rpm, 4° C., 20 min, each plasma sample was collected. Then, 10 μL of the plasma was added to 2 ml of DMSO, and the fluorescence intensity of HPMA-PP at 635 to 660 nm was measured by a fluorescence spectrophotometer with excitation at 420 nm, and the time course change of the concentration of HPMA-PP in plasma was measured. The result shows that HPMA-PP is more than several ten folds higher plasma concentration than free PP (see FIG. 11*a*).

In a similar manner to the above, HPMA-ZnPP was treated, the fluorescence intensity of HPMA-ZnPP at 580 to 660 nm was measured, and the time course change of the concentration of HPMA-ZnPP in plasma was measured. The result shows that HPMA-ZnPP is more than several ten folds higher plasma concentration than free ZnPP (see FIG. 11*b*).

<Example 6> Preparation of Rhodamine Conjugated Albumin

Firstly, 100 mg of human serum albumin was dissolved in 0.1M $NaHCO_3$, and the pH was adjusted to 8.0 to 9.0 under stirring with a magnetic stirrer. To this solution was added 20 mg of fluorescence dye, tetramethylrhodamine isothiocyanate (TRITC; Sigma-Aldrich, St. Louis, Mo.) or the like at room temperature, and stirred. The reaction was continued for 5 to 6 hours, or if more extensive labeling was desired, the reaction was continued for 20 hours at pH>8.5. To remove decomposition products and unreacted materials, the reaction mixture was dialyzed with distilled water by a conventional procedure. Alternatively, the reaction mixture was subjected to chromatography using Sephadex G-25 or G-50 column (Φ3.0 to 5.0 cm×L 70 to 80 cm) with distilled water as an eluant. The fluorescent labeled protein desalted by a dialysis fluid inside or Sephadex was collected, followed by lyophilization of the product to obtain a desired complex (yield: about 98 mg).

<Example 7> Fluorescent Tumor Detection by Using Fluorescent Molecular Probes

Both side of dorsal skin of ddY mice were inoculated with each site with $10^6$ 5180 tumor cells. When this tumor become palpable size (5 to 8 mm) in diameter, rhodamine bound albumin (200 mg/kg) obtained in Example 7 or SMA-ICG micelle (30 mg/kg) obtained in Example 2 was injected intravenously. Fluorescent image was observed after 15 hours and the results are shown in FIG. 3.

In FIG. 3, (A) shows the fluorescence image of tumor bearing mouse injected with rhodamine conjugated albumin (excitation light: 535 nm±15 nm, fluorescence was observed with a band path filter of 600 nm±10 nm), and (B) shows the fluorescence image of tumor bearing mouse injected with SMA-ICG (excitation light: 710 nm±15 nm, fluorescence image was observed with a band path filter of 800 nm±10 nm).

<Example 8> Generation of Singlet Oxygen [$^1O_2$] from Rose Bengal Upon Irradiation Generation of singlet oxygen [$^1O_2$] from rose bengal upon irradiation was demonstrated by ESR (electron spin resonance) spectroscopy. Detection of $^1O_2$ radical was carried out using spin trapping agent TEMP (2,2,6,6-tetramethylpiperidine, Wako Pure Chem. Inc., Osaka, Japan). TEMP is generally used spin trapping agent for trapping singlet oxygen and forms its $^1O_2$ adduct, which exhibits [$^1O_2$] specific triplet signal to be detected upon ESR (electron spin resonance) spectroscopy.

To a physiological saline containing SMA-rose bengal (SMA-RB) micelle obtained in Example 3 or free rose bengal at 33.0 μM was added TEMP at 30 mM, and light irradiation was performed as follows, and ESR spectra were obtained.

The measurement of ESR was carried out using X-band type ESR measurement instrument (JEOL Co. Ltd, Tokyo, Model FA 100), at microwave power of 4.0 mW, amplitude of 200 KHz, and modulation width of 0.1[mT]. Light irradiation was carried out using xenon lamp 650W (Master Projector Co., Model Master Lux-S, Rikagaku Seiki Co. Ltd, Tokyo) at 10 cm distance from the lens orifice while cooling with an air blower.

As shown in FIG. 12, similar to free RB, SMA-RB micelle also generates singlet oxygen, of which the intensity was increased in an irradiation time dependent manner. In contrast, free RB showed clear decrease after ten min, and ceased generation of singlet oxygen completely after 20 min or longer irradiation and thus [$^1O_2$] became undetectable. This suggests that free RB is rapidly decomposed by light irradiation. From the results, it is evident that SMA-RB micelle can stably generate singlet oxygen for longer time than free RB, which is about ten times more stable than free RB, and thus SMA-RB micelle is highly useful compared with free RB. Such generation of singlet oxygen in tumors induces apoptotic or necrotic cell death of tumor cells by the reaction of singlet oxygen with tumor cells, and hence antitumor effect is expected.

<Example 9> Cytotoxic Effect of SMA-MB Micelle on Human Pancreatic Cancer Cell Line PC1.0 Cells Human pancreatic cancer cells PC1.0 were plated in 96 well culture plate at 1000 cells/well and cultured overnight. Then, methylene blue (MB) or SMA-methylene blue (SMA-MB) micelle was added to the cultured cells above, and allowed to culture another 48 hours. Light irradiation was carried out using tungsten xenon lamp at 15 cm distance from the cell surface for 20 min. Then, the survival rate of the cells was quantified by MTT Method. The results show that the cytotoxic effect was significantly increased by light exposure in both groups. The results are shown in FIG. 13 and Table 1.

TABLE 1

| Cell lines | Test samples | Light irradiation | $IC_{50}$ (μM) |
|---|---|---|---|
| PC1.0 (human pancreatic cancer cell line) | Methylene blue | None | 4.5 |
| | | 20 min | 0.5 |
| | SMA-methylene blue micelle | None | 5.5 |
| | | 20 min | 0.1 |

The invention claimed is:

1. A complex comprising a fluorescent molecule and a biocompatible macromolecule, wherein the fluorescent molecule is chlorophyll, the biocompatible macromolecule is selected from styrene-maleic acid copolymers, styrene-maleic acid copolymers having a multiple-functionalized maleic acid side chain, and mixtures thereof, the fluorescent molecule is non-covalently bound to the biocompatible macromolecule, and the complex is in the form of a micelle in which the fluorescent molecule is encapsulated in the biocompatible macromolecule.

2. A macromolecular fluorescent molecular probe for fluorescent detection of tumor, comprising the complex according to claim 1.

3. The macromolecular fluorescent molecular probe according to claim 2, which is for fluorescent detection of tumor by using a fluorescent endoscope or a fluorescent laparoscope.

4. The complex according to claim 1, wherein the fluorescent molecule is chlorophyll, and the biocompatible macromolecule is selected from styrene-maleic acid copolymers.

5. A macromolecular fluorescent molecular probe for fluorescent detection of tumor, comprising the complex according to claim 4.

6. The macromolecular fluorescent molecular probe according to claim 5, which is for fluorescent detection of tumor by using a fluorescent endoscope or a fluorescent laparoscope.

* * * * *